US009555186B2

(12) United States Patent
Kruse

(10) Patent No.: US 9,555,186 B2
(45) Date of Patent: Jan. 31, 2017

(54) INFUSION PUMP SYSTEM WITH DISPOSABLE CARTRIDGE HAVING PRESSURE VENTING AND PRESSURE FEEDBACK

(71) Applicant: Tandem Diabetes Care, Inc., San Diego, CA (US)

(72) Inventor: Geoffrey A. Kruse, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 704 days.

(21) Appl. No.: 13/838,617

(22) Filed: Mar. 15, 2013

(65) Prior Publication Data
US 2013/0324928 A1    Dec. 5, 2013

Related U.S. Application Data

(60) Provisional application No. 61/655,883, filed on Jun. 5, 2012.

(51) Int. Cl.
*A61M 5/142* (2006.01)
*A61M 5/168* (2006.01)
*A61M 5/148* (2006.01)

(52) U.S. Cl.
CPC ............. *A61M 5/142* (2013.01); *A61M 5/148* (2013.01); *A61M 5/14244* (2013.01); *A61M 5/16854* (2013.01); *A61M 5/16881* (2013.01); *A61M 2205/12* (2013.01); *A61M 2205/3331* (2013.01)

(58) Field of Classification Search
CPC .............. A61M 5/142; A61M 5/16854; A61M 5/14244; A61M 2205/3331; A61M 2205/12; A61M 2205/128
See application file for complete search history.

(56) References Cited

U.S. PATENT DOCUMENTS

| 722,431 A | 3/1903 | Packard |
| 1,079,522 A | 11/1913 | Smith |
| 1,274,884 A | 8/1918 | Hudson |
| 1,314,987 A | 9/1919 | Smith |

(Continued)

FOREIGN PATENT DOCUMENTS

| EP | 0272530 | 6/1988 |
| GB | 2159496 | 12/1985 |

(Continued)

OTHER PUBLICATIONS

International Search Report for International Application No. PCT/US2003/022703 dated Sep. 10, 2004.

(Continued)

*Primary Examiner* — Nathan R Price
*Assistant Examiner* — Melissa A Snyder
(74) *Attorney, Agent, or Firm* — Patterson Thuente Pedersen, P.A.

(57) ABSTRACT

Systems and methods of venting a cartridge of an infusion pump system are disclosed. The system can be actively vented. A interior volume of the system can be actively vented at times when a drive mechanism of the system is inactive. Such an active venting system can include a valve that seals a volume of the cartridge that can be vented from the ambient when pressure measurements in the cartridge are made by a pressure sensor for greater measurement and calculation accuracy.

20 Claims, 14 Drawing Sheets

(56) References Cited

U.S. PATENT DOCUMENTS

| | | |
|---|---|---|
| 1,866,061 A | 7/1932 | Schoel |
| 2,398,234 A | 4/1946 | Long |
| 2,412,397 A | 12/1946 | Harper |
| 2,736,463 A | 2/1956 | Michael |
| 2,971,466 A | 2/1961 | Corbett |
| 3,017,903 A | 1/1962 | Steffens |
| 3,023,750 A | 3/1962 | Baron |
| 3,133,678 A | 5/1964 | Marwell et al. |
| 3,153,414 A | 10/1964 | Beall et al. |
| 3,187,562 A | 6/1965 | Rolfson |
| 3,202,178 A | 8/1965 | Milton |
| 3,227,311 A | 1/1966 | Rowell |
| 3,302,578 A | 2/1967 | Anderson |
| 3,318,138 A | 5/1967 | Rolfson |
| 3,347,418 A | 10/1967 | Fefferman |
| 3,455,147 A | 7/1969 | Peck et al. |
| 3,493,496 A | 2/1970 | Bray et al. |
| 3,583,603 A | 6/1971 | Freckmann et al. |
| 3,596,939 A | 8/1971 | Gibson |
| 3,648,694 A | 3/1972 | Mogos et al. |
| 3,654,959 A | 4/1972 | Kassel |
| 3,673,853 A | 7/1972 | Griswold et al. |
| 3,724,234 A | 4/1973 | Garavelli |
| 3,756,459 A | 9/1973 | Bannister et al. |
| 3,838,794 A | 10/1974 | Cogley et al. |
| 3,894,538 A | 7/1975 | Richter |
| RE28,890 E | 7/1976 | Ingram et al. |
| 3,985,133 A | 10/1976 | Jenkins et al. |
| 4,028,931 A | 6/1977 | Bisera et al. |
| 4,087,301 A | 5/1978 | Steadman |
| 4,089,206 A | 5/1978 | Raffel et al. |
| 4,106,510 A | 8/1978 | Hakim et al. |
| 4,137,913 A | 2/1979 | Georgi |
| 4,191,184 A | 3/1980 | Carlisle |
| 4,250,872 A | 2/1981 | Tamari |
| 4,265,241 A | 5/1981 | Portner et al. |
| 4,271,989 A | 6/1981 | O'Neill |
| 4,314,979 A | 2/1982 | Deabriges |
| 4,327,845 A | 5/1982 | Keyes et al. |
| 4,330,071 A | 5/1982 | Ohlson |
| 4,403,984 A | 9/1983 | Ash et al. |
| 4,405,294 A | 9/1983 | Albarda |
| 4,416,596 A | 11/1983 | Lichtenstein |
| 4,440,323 A | 4/1984 | Benson |
| 4,443,218 A | 4/1984 | DeCant et al. |
| 4,445,885 A | 5/1984 | Kifune |
| 4,481,808 A | 11/1984 | Sakata et al. |
| 4,520,948 A | 6/1985 | Hampel et al. |
| 4,529,106 A | 7/1985 | Broadfoot et al. |
| 4,538,616 A | 9/1985 | Rogoff |
| 4,557,726 A | 12/1985 | Reinicke |
| 4,624,661 A | 11/1986 | Arimond |
| 4,636,226 A | 1/1987 | Canfora |
| 4,666,430 A | 5/1987 | Brown et al. |
| 4,673,415 A | 6/1987 | Stanford |
| 4,678,460 A | 7/1987 | Rosner |
| 4,684,367 A | 8/1987 | Schaffer et al. |
| 4,718,430 A | 1/1988 | Holzer |
| 4,718,893 A | 1/1988 | Dorman et al. |
| 4,741,736 A | 5/1988 | Brown |
| 4,779,762 A | 10/1988 | Klein et al. |
| 4,808,167 A | 2/1989 | Mann et al. |
| 4,810,243 A | 3/1989 | Howson |
| 4,826,482 A | 5/1989 | Kamen |
| 4,878,896 A | 11/1989 | Garrison et al. |
| 4,886,499 A | 12/1989 | Cirelli et al. |
| 4,893,966 A | 1/1990 | Roehl |
| 4,902,278 A | 2/1990 | Maget et al. |
| 4,908,017 A | 3/1990 | Howson et al. |
| 4,936,832 A | 6/1990 | Vaillancourt |
| 4,955,860 A | 9/1990 | Ruano |
| 4,969,884 A | 11/1990 | Yum |
| 4,976,162 A | 12/1990 | Kamen |
| 5,005,403 A | 4/1991 | Steudle et al. |
| 5,038,821 A | 8/1991 | Maget |
| 5,059,182 A | 10/1991 | Laing |
| 5,062,834 A | 11/1991 | Gross |
| 5,090,963 A | 2/1992 | Gross et al. |
| 5,096,385 A | 3/1992 | Georgi et al. |
| 5,104,813 A | 4/1992 | Besemer et al. |
| 5,131,816 A | 7/1992 | Brown et al. |
| 5,154,712 A | 10/1992 | Herweck et al. |
| 5,170,912 A | 12/1992 | Du |
| 5,178,603 A | 1/1993 | Prince |
| 5,188,258 A | 2/1993 | Iwashita |
| 5,192,272 A | 3/1993 | Faure |
| 5,207,645 A | 5/1993 | Ross et al. |
| 5,215,450 A | 6/1993 | Tamari |
| 5,241,935 A | 9/1993 | Beck et al. |
| 5,247,434 A | 9/1993 | Peterson et al. |
| 5,256,157 A | 10/1993 | Samiotes et al. |
| 5,295,976 A | 3/1994 | Harris |
| 5,328,464 A | 7/1994 | Kriesel et al. |
| 5,334,162 A | 8/1994 | Harris |
| 5,335,705 A | 8/1994 | Morishita et al. |
| 5,336,180 A | 8/1994 | Kriesel et al. |
| 5,336,188 A | 8/1994 | Kriesel |
| 5,337,747 A | 8/1994 | Neftel |
| 5,341,783 A | 8/1994 | Beck et al. |
| 5,354,273 A | 10/1994 | Hagen |
| 5,364,242 A | 11/1994 | Olsen |
| 5,399,166 A | 3/1995 | Laing |
| 5,419,770 A | 5/1995 | Crass et al. |
| 5,421,208 A | 6/1995 | Packard et al. |
| 5,423,743 A | 6/1995 | Butterfield |
| 5,431,171 A | 7/1995 | Harrison et al. |
| 5,431,627 A | 7/1995 | Pastrone et al. |
| 5,466,229 A | 11/1995 | Elson et al. |
| 5,476,449 A | 12/1995 | Richmond |
| 5,492,534 A | 2/1996 | Athayde et al. |
| 5,503,538 A | 4/1996 | Wiernicki et al. |
| 5,505,709 A | 4/1996 | Funderburk et al. |
| 5,518,730 A | 5/1996 | Fuisz |
| 5,527,288 A | 6/1996 | Gross et al. |
| 5,531,697 A | 7/1996 | Olsen et al. |
| 5,531,698 A | 7/1996 | Olsen |
| 5,544,519 A | 8/1996 | Hammarberg et al. |
| 5,551,391 A | 9/1996 | Beck et al. |
| 5,551,850 A | 9/1996 | Williamson et al. |
| 5,568,806 A | 10/1996 | Cheney, II et al. |
| 5,575,310 A | 11/1996 | Kamen et al. |
| 5,593,552 A | 1/1997 | Joshi et al. |
| RE35,501 E | 5/1997 | Ross et al. |
| 5,639,220 A | 6/1997 | Hayakawa |
| 5,647,854 A | 7/1997 | Olsen et al. |
| 5,656,032 A | 8/1997 | Kriesel et al. |
| 5,669,877 A | 9/1997 | Blomquist |
| 5,700,244 A | 12/1997 | Kriesel |
| 5,704,520 A * | 1/1998 | Gross .......................... 222/334 |
| 5,735,818 A | 4/1998 | Kriesel et al. |
| 5,741,242 A | 4/1998 | Kriesel |
| 5,755,683 A | 5/1998 | Houle et al. |
| 5,763,267 A | 6/1998 | Kurjan et al. |
| 5,785,688 A | 7/1998 | Joshi et al. |
| 5,810,771 A | 9/1998 | Blomquist |
| 5,840,071 A | 11/1998 | Kriesel et al. |
| 5,840,770 A | 11/1998 | Hill |
| 5,858,201 A | 1/1999 | Otsuka et al. |
| 5,860,957 A | 1/1999 | Jacobsen et al. |
| 5,873,857 A | 2/1999 | Kriesel |
| 5,885,250 A | 3/1999 | Kriesel et al. |
| 5,891,097 A | 4/1999 | Saito et al. |
| 5,897,530 A | 4/1999 | Jackson |
| 5,902,336 A | 5/1999 | Mishkin |
| 5,924,448 A | 7/1999 | West |
| 5,935,099 A | 8/1999 | Peterson et al. |
| 5,938,636 A | 8/1999 | Kramer |
| 5,938,640 A | 8/1999 | Maget et al. |
| 5,944,694 A | 8/1999 | Hitchins |
| 5,948,367 A | 9/1999 | Gmeiner et al. |
| 5,951,523 A | 9/1999 | Osterlind et al. |
| 5,954,696 A | 9/1999 | Ryan |
| 5,954,700 A | 9/1999 | Kovelman |
| 5,961,305 A | 10/1999 | Eek et al. |

(56) References Cited

U.S. PATENT DOCUMENTS

| | | |
|---|---|---|
| 5,962,794 A | 10/1999 | Kriesel et al. |
| 5,980,489 A | 11/1999 | Kriesel |
| 5,984,894 A | 11/1999 | Poulsen et al. |
| 5,997,501 A | 12/1999 | Gross et al. |
| 6,013,020 A | 1/2000 | Meloul et al. |
| 6,063,059 A | 5/2000 | Kriesel |
| 6,077,246 A | 6/2000 | Kullas et al. |
| 6,086,561 A | 7/2000 | Kriesel et al. |
| 6,093,312 A | 7/2000 | Boulter |
| 6,105,442 A | 8/2000 | Kriesel et al. |
| RE36,871 E | 9/2000 | Epstein et al. |
| 6,123,686 A | 9/2000 | Olsen et al. |
| D433,755 S | 11/2000 | Mastrototaro et al. |
| 6,152,898 A | 11/2000 | Olsen |
| 6,165,155 A | 12/2000 | Jacobsen et al. |
| 6,186,982 B1 | 2/2001 | Gross et al. |
| 6,202,708 B1 | 3/2001 | Bynum |
| 6,213,120 B1 | 4/2001 | Block et al. |
| 6,217,826 B1 | 4/2001 | Reeder et al. |
| 6,223,746 B1 | 5/2001 | Jewett et al. |
| 6,232,609 B1 | 5/2001 | Snyder et al. |
| 6,236,887 B1 | 5/2001 | Ben-Haim et al. |
| 6,241,704 B1 | 6/2001 | Peterson et al. |
| 6,251,293 B1 | 6/2001 | Snodgrass et al. |
| 6,251,932 B1 | 6/2001 | Reichelt et al. |
| 6,254,569 B1 | 7/2001 | O'Donnell et al. |
| 6,280,408 B1 | 8/2001 | Sipin |
| 6,280,409 B1 | 8/2001 | Stone |
| 6,283,680 B1 | 9/2001 | Vidal |
| 6,293,159 B1 | 9/2001 | Kriesel et al. |
| 6,293,429 B2 | 9/2001 | Sadler et al. |
| 6,298,760 B1 | 10/2001 | Truttmann et al. |
| 6,302,653 B1 | 10/2001 | Bryant et al. |
| 6,302,855 B1 | 10/2001 | Lav et al. |
| 6,331,172 B1 | 12/2001 | Epstein et al. |
| 6,340,783 B1 | 1/2002 | Snow |
| 6,368,314 B1 | 4/2002 | Kipfer et al. |
| 6,372,182 B1 | 4/2002 | Mauro et al. |
| 6,372,508 B1 | 4/2002 | Shnizer et al. |
| 6,374,876 B2 | 4/2002 | Bynum |
| 6,382,923 B1 | 5/2002 | Gray |
| 6,398,760 B1 | 6/2002 | Danby |
| 6,406,455 B1 | 6/2002 | Willis et al. |
| 6,413,238 B1 | 7/2002 | Maget |
| 6,416,293 B1 | 7/2002 | Bouchard et al. |
| 6,420,160 B1 | 7/2002 | Bloch |
| 6,425,740 B1 | 7/2002 | Jacobsen et al. |
| 6,458,102 B1 | 10/2002 | Mann et al. |
| 6,475,180 B2 | 11/2002 | Peterson et al. |
| 6,485,263 B1 | 11/2002 | Bryant et al. |
| 6,520,936 B1 | 2/2003 | Mann |
| 6,537,268 B1 | 3/2003 | Gibson et al. |
| 6,537,272 B2 | 3/2003 | Christopherson et al. |
| 6,542,775 B2 | 4/2003 | Ding et al. |
| 6,544,212 B2 | 4/2003 | Galley et al. |
| 6,551,276 B1 | 4/2003 | Mann et al. |
| 6,562,001 B2 | 5/2003 | Lebel et al. |
| 6,571,128 B2 | 5/2003 | Lebel et al. |
| 6,577,899 B2 | 6/2003 | Lebel et al. |
| 6,582,393 B2 | 6/2003 | Sage, Jr. |
| 6,585,695 B1 | 7/2003 | Adair et al. |
| 6,604,908 B1 | 8/2003 | Bryant et al. |
| 6,605,072 B2 | 8/2003 | Struys et al. |
| 6,610,003 B1 | 8/2003 | Meloul et al. |
| 6,623,698 B2 | 9/2003 | Kuo |
| 6,641,533 B2 | 11/2003 | Causey, III et al. |
| 6,641,562 B1 | 11/2003 | Peterson |
| 6,642,019 B1 | 11/2003 | Anderson et al. |
| 6,648,821 B2 | 11/2003 | Lebel et al. |
| 6,656,158 B2 | 12/2003 | Gregory et al. |
| 6,663,359 B2 | 12/2003 | Gray |
| 6,666,021 B1 | 12/2003 | Lewis |
| 6,668,196 B1 | 12/2003 | Villegas et al. |
| 6,676,387 B1 | 1/2004 | Penn |
| 6,683,690 B1 | 1/2004 | Tobias |
| 6,740,059 B2 | 5/2004 | Flaherty |
| 6,740,075 B2 | 5/2004 | Lebel et al. |
| 6,743,201 B1 | 6/2004 | Donig et al. |
| 6,743,202 B2 | 6/2004 | Hirschman et al. |
| 6,745,079 B2 | 6/2004 | King |
| 6,749,403 B2 | 6/2004 | Spencer et al. |
| 6,749,587 B2 | 6/2004 | Flaherty |
| 6,752,785 B2 | 6/2004 | Van Antwerp et al. |
| 6,752,787 B1 | 6/2004 | Causey, III et al. |
| 6,755,828 B2 | 6/2004 | Shevtsov et al. |
| 6,758,593 B1 | 7/2004 | Terentiev |
| 6,767,188 B2 | 7/2004 | Vrane et al. |
| 6,767,896 B1 | 7/2004 | McIntosh |
| 6,773,669 B1 | 8/2004 | Holaday et al. |
| 6,776,776 B2 | 8/2004 | Alchas et al. |
| 6,780,156 B2 | 8/2004 | Haueter et al. |
| 6,780,171 B2 | 8/2004 | Gabel et al. |
| 6,780,426 B2 | 8/2004 | Zhang et al. |
| 6,780,770 B2 | 8/2004 | Larson |
| 6,780,836 B2 | 8/2004 | Unemori |
| 6,783,107 B2 | 8/2004 | Chatufale |
| 6,783,328 B2 | 8/2004 | Lucke et al. |
| 6,790,670 B2 | 9/2004 | Munagavalasa et al. |
| 6,796,956 B2 | 9/2004 | Hartlaub et al. |
| 6,804,002 B2 | 10/2004 | Fikhte et al. |
| 6,804,555 B2 | 10/2004 | Warkentin |
| 6,805,122 B2 | 10/2004 | Richey, II et al. |
| 6,808,506 B2 | 10/2004 | Lastovich et al. |
| 6,809,653 B1 | 10/2004 | Mann et al. |
| 6,810,290 B2 | 10/2004 | Lebel et al. |
| RE38,654 E | 11/2004 | Hill et al. |
| 6,811,534 B2 | 11/2004 | Bowman et al. |
| 6,811,792 B2 | 11/2004 | Roser et al. |
| 6,813,519 B2 | 11/2004 | Lebel et al. |
| 6,813,964 B1 | 11/2004 | Clark et al. |
| 6,821,249 B2 | 11/2004 | Casscells et al. |
| 6,821,484 B1 | 11/2004 | Gregersen |
| 6,824,529 B2 | 11/2004 | Gross et al. |
| 6,827,524 B2 | 12/2004 | Starry, Jr. et al. |
| 6,827,702 B2 | 12/2004 | Lebel et al. |
| 6,827,710 B1 | 12/2004 | Mooney et al. |
| 6,827,898 B1 | 12/2004 | Fausset et al. |
| 6,828,552 B2 | 12/2004 | Hartley |
| 6,830,560 B2 | 12/2004 | Gross et al. |
| 6,835,175 B1 | 12/2004 | Porumbescu |
| 6,835,194 B2 | 12/2004 | Johnson et al. |
| 6,842,042 B2 | 1/2005 | Tetelbaum |
| 6,843,782 B2 | 1/2005 | Gross et al. |
| 6,847,898 B1 | 1/2005 | Chen et al. |
| 6,852,104 B2 | 2/2005 | Blomquist |
| 6,852,487 B1 | 2/2005 | Barany et al. |
| 6,854,020 B1 | 2/2005 | Kamihara |
| 6,854,432 B2 | 2/2005 | Hirano |
| 6,858,011 B2 | 2/2005 | Sehgal |
| 6,858,403 B2 | 2/2005 | Han et al. |
| 6,864,101 B1 | 3/2005 | Winkler et al. |
| 6,867,196 B1 | 3/2005 | Wolff et al. |
| 6,868,358 B2 | 3/2005 | Brown, Jr. |
| 6,872,200 B2 | 3/2005 | Mann et al. |
| 6,873,268 B2 | 3/2005 | Lebel et al. |
| 6,876,885 B2 | 4/2005 | Swoyer et al. |
| 6,877,713 B1 | 4/2005 | Gray et al. |
| 6,880,564 B2 | 4/2005 | Erickson |
| 6,884,122 B2 | 4/2005 | Robinson et al. |
| 6,884,228 B2 | 4/2005 | Brown et al. |
| 6,885,888 B2 | 4/2005 | Rezai |
| 6,886,556 B2 | 5/2005 | Fuchs |
| 6,892,755 B2 | 5/2005 | Black |
| 6,892,900 B2 | 5/2005 | Drechsel |
| 6,894,024 B2 | 5/2005 | Coolidge et al. |
| 6,896,666 B2 | 5/2005 | Kochamba |
| RE38,749 E | 6/2005 | Dardik |
| 6,905,479 B1 | 6/2005 | Bouchard et al. |
| 6,906,028 B2 | 6/2005 | Defelippis et al. |
| 6,908,591 B2 | 6/2005 | Macphee et al. |
| 6,909,840 B2 | 6/2005 | Harwig et al. |
| 6,912,425 B2 | 6/2005 | Nova et al. |
| 6,913,933 B2 | 7/2005 | Jacobs et al. |
| 6,914,076 B2 | 7/2005 | Cavazza |

(56) References Cited

U.S. PATENT DOCUMENTS

| | | |
|---|---|---|
| 6,916,159 B2 | 7/2005 | Rush et al. |
| 6,923,006 B2 | 8/2005 | Walton |
| 6,923,180 B2 | 8/2005 | Richey et al. |
| 6,923,764 B2 | 8/2005 | Aceti et al. |
| 6,926,694 B2 | 8/2005 | Marano-Ford et al. |
| 6,930,093 B2 | 8/2005 | Brantl |
| 6,931,845 B2 | 8/2005 | Schaeffer |
| 6,931,925 B2 | 8/2005 | Huemer et al. |
| 6,932,114 B2 | 8/2005 | Sparks |
| 6,932,796 B2 | 8/2005 | Sage et al. |
| 6,935,539 B2 | 8/2005 | Krieger et al. |
| 6,936,026 B2 | 8/2005 | Diermann et al. |
| 6,936,046 B2 | 8/2005 | Hissong et al. |
| 6,939,323 B2 | 9/2005 | Angel et al. |
| 6,939,324 B2 | 9/2005 | Gonnelli et al. |
| 6,942,636 B2 | 9/2005 | Holst et al. |
| 6,943,034 B1 | 9/2005 | Winkler et al. |
| 6,946,117 B1 | 9/2005 | Schutt et al. |
| 6,949,081 B1 | 9/2005 | Chance |
| 6,950,708 B2 | 9/2005 | Bowman et al. |
| 6,951,165 B2 | 10/2005 | Kuhn et al. |
| 6,951,553 B2 | 10/2005 | Bubb et al. |
| 6,952,963 B2 | 10/2005 | Delnevo |
| 6,955,819 B2 | 10/2005 | Zhang et al. |
| 6,955,915 B2 | 10/2005 | Fodor et al. |
| 6,956,204 B2 | 10/2005 | Dong et al. |
| 6,957,655 B2 | 10/2005 | Erickson et al. |
| 6,957,924 B1 | 10/2005 | McKeekin et al. |
| 6,958,073 B2 | 10/2005 | Rogers et al. |
| 6,958,705 B2 | 10/2005 | Lebel et al. |
| 6,960,184 B2 | 11/2005 | Willis et al. |
| 6,960,192 B1 | 11/2005 | Flaherty et al. |
| 6,962,103 B2 | 11/2005 | Sandlin |
| 6,962,151 B1 | 11/2005 | Knoch et al. |
| 6,963,770 B2 | 11/2005 | Scarantino et al. |
| 6,964,356 B2 | 11/2005 | Kim |
| 6,966,325 B2 | 11/2005 | Erickson |
| 6,969,369 B2 | 11/2005 | Struble |
| 6,970,741 B1 | 11/2005 | Whitehurst et al. |
| 6,970,742 B2 | 11/2005 | Mann et al. |
| 6,971,999 B2 | 12/2005 | Py et al. |
| 6,974,055 B2 | 12/2005 | Moore et al. |
| 6,974,115 B2 | 12/2005 | Silva |
| 6,974,437 B2 | 12/2005 | Lebel et al. |
| 6,974,588 B1 | 12/2005 | Miranda et al. |
| 6,979,308 B1 | 12/2005 | MacDonald et al. |
| 6,979,316 B1 | 12/2005 | Rubin et al. |
| 6,980,855 B2 | 12/2005 | Cho |
| 6,981,499 B2 | 1/2006 | Anderson et al. |
| 6,981,967 B2 | 1/2006 | Massengale et al. |
| 6,982,248 B2 | 1/2006 | Coolidge et al. |
| 6,985,770 B2 | 1/2006 | Nyhart |
| 6,985,771 B2 | 1/2006 | Fischell et al. |
| 6,986,867 B2 | 1/2006 | Hanley et al. |
| 6,987,129 B2 | 1/2006 | Mak et al. |
| 6,991,619 B2 | 1/2006 | Marano-Ford et al. |
| 6,991,620 B2 | 1/2006 | Marano-Ford et al. |
| 6,994,700 B2 | 2/2006 | Elkins et al. |
| 6,997,911 B2 | 2/2006 | Klitmose |
| 6,997,920 B2 | 2/2006 | Mann et al. |
| 6,998,387 B1 | 2/2006 | Goke et al. |
| 6,998,404 B2 | 2/2006 | Moskowitz |
| 6,999,854 B2 | 2/2006 | Roth |
| 7,004,928 B2 | 2/2006 | Aceti et al. |
| 7,008,399 B2 | 3/2006 | Larsen et al. |
| 7,008,403 B1 | 3/2006 | Mallett |
| 7,010,340 B2 | 3/2006 | Scarantino et al. |
| 7,013,727 B2 | 3/2006 | Delnevo |
| 7,015,782 B2 | 3/2006 | Kincaid et al. |
| 7,018,360 B2 | 3/2006 | Flaherty et al. |
| 7,018,361 B2 | 3/2006 | Gillespie et al. |
| 7,022,072 B2 | 4/2006 | Fox et al. |
| 7,022,087 B2 | 4/2006 | Dempster et al. |
| 7,022,108 B2 | 4/2006 | Marano-Ford et al. |
| 7,024,244 B2 | 4/2006 | Muhlenberg et al. |
| 7,024,245 B2 | 4/2006 | Lebel et al. |
| 7,025,716 B1 | 4/2006 | Meloul et al. |
| 7,029,455 B2 * | 4/2006 | Flaherty ........................ 604/131 |
| 7,033,338 B2 | 4/2006 | Vilks et al. |
| 7,033,843 B2 | 4/2006 | Hasegawa et al. |
| 7,041,082 B2 | 5/2006 | Blomquist et al. |
| 7,047,070 B2 | 5/2006 | Wilkinson et al. |
| 7,048,193 B2 | 5/2006 | Tsukada et al. |
| 7,048,951 B1 | 5/2006 | Seitz et al. |
| 7,052,251 B2 | 5/2006 | Nason et al. |
| 7,053,761 B2 | 5/2006 | Schofield et al. |
| 7,056,302 B2 | 6/2006 | Douglas |
| 7,056,494 B2 | 6/2006 | Adjei et al. |
| 7,056,887 B2 | 6/2006 | Coolidge et al. |
| 7,059,348 B2 | 6/2006 | Nat |
| 7,060,856 B2 | 6/2006 | Macikenas et al. |
| 7,064,472 B2 | 6/2006 | Pelrine et al. |
| 7,066,359 B2 | 6/2006 | Greiner-Perth |
| 7,066,910 B2 | 6/2006 | Bauhahn et al. |
| 7,066,915 B2 | 6/2006 | Olsen |
| 7,066,922 B2 | 6/2006 | Angel et al. |
| 7,069,075 B2 | 6/2006 | Olson |
| 7,070,577 B1 | 7/2006 | Haller et al. |
| 7,072,802 B2 | 7/2006 | Hartlaub |
| 7,073,485 B2 | 7/2006 | Truscott et al. |
| 7,077,822 B1 | 7/2006 | Howard, III |
| 7,078,163 B2 | 7/2006 | Torrianni et al. |
| 7,082,812 B2 | 8/2006 | Lenormand et al. |
| 7,083,592 B2 | 8/2006 | Lastovich et al. |
| 7,083,599 B2 | 8/2006 | Alchas et al. |
| 7,095,210 B2 | 8/2006 | Tamura et al. |
| 7,098,803 B2 | 8/2006 | Mann et al. |
| 7,104,981 B2 | 9/2006 | Elkins et al. |
| 7,107,706 B1 | 9/2006 | Bailey et al. |
| 7,108,491 B2 | 9/2006 | Ganser |
| 7,108,679 B2 | 9/2006 | Alchas |
| 7,109,878 B2 | 9/2006 | Mann et al. |
| 7,111,346 B2 | 9/2006 | Inman et al. |
| 7,115,108 B2 | 10/2006 | Wilkinson et al. |
| 7,118,351 B2 | 10/2006 | Effenhauser et al. |
| 7,118,676 B2 | 10/2006 | Mueth et al. |
| 7,122,151 B2 | 10/2006 | Reeder et al. |
| 7,127,292 B2 | 10/2006 | Warman et al. |
| 7,128,727 B2 | 10/2006 | Flaherty et al. |
| 7,128,730 B2 | 10/2006 | Marano-Ford et al. |
| 7,136,701 B2 | 11/2006 | Greatbatch et al. |
| 7,137,964 B2 | 11/2006 | Flaherty |
| 7,138,141 B2 | 11/2006 | Platz et al. |
| 7,141,425 B2 | 11/2006 | Dzekunov et al. |
| 7,144,384 B2 | 12/2006 | Gorman et al. |
| 7,144,729 B2 | 12/2006 | Rolland et al. |
| 7,147,386 B2 | 12/2006 | Zhang et al. |
| 7,147,839 B2 | 12/2006 | Sampath et al. |
| 7,150,726 B2 | 12/2006 | Dalton |
| 7,150,737 B2 | 12/2006 | Purdy et al. |
| 7,150,741 B2 | 12/2006 | Erickson et al. |
| 7,152,673 B2 | 12/2006 | Lohbeck et al. |
| 7,153,286 B2 | 12/2006 | Busby et al. |
| 7,153,823 B2 | 12/2006 | Franco |
| 7,156,808 B2 | 1/2007 | Quy |
| 7,159,271 B2 | 1/2007 | Sepke et al. |
| 7,162,303 B2 | 1/2007 | Levin et al. |
| 7,163,385 B2 | 1/2007 | Gharib et al. |
| 7,163,520 B2 | 1/2007 | Bernard |
| 7,189,352 B2 | 3/2007 | Carpenter et al. |
| 7,193,521 B2 | 3/2007 | Moberg et al. |
| 7,194,890 B2 | 3/2007 | Tanaka et al. |
| 7,195,616 B2 | 3/2007 | Diller et al. |
| 7,198,603 B2 | 4/2007 | Penner et al. |
| 7,198,637 B2 | 4/2007 | Deshmukh et al. |
| 7,198,751 B2 | 4/2007 | Carpenter et al. |
| 7,198,940 B2 | 4/2007 | Vellinger et al. |
| 7,201,730 B2 | 4/2007 | Davidner et al. |
| 7,204,823 B2 | 4/2007 | Estes et al. |
| 7,204,958 B2 | 4/2007 | Olsen et al. |
| 7,207,952 B2 | 4/2007 | Takinami et al. |
| 7,207,964 B2 | 4/2007 | Davidner et al. |
| 7,208,120 B2 | 4/2007 | Bitensky et al. |
| 7,214,207 B2 | 5/2007 | Lynch et al. |

(56) References Cited

U.S. PATENT DOCUMENTS

| | | |
|---|---|---|
| 7,214,221 B2 | 5/2007 | Fentress et al. |
| 7,214,658 B2 | 5/2007 | Tobinick |
| 7,217,699 B2 | 5/2007 | Yakubov |
| 7,217,796 B2 | 5/2007 | Wang et al. |
| 7,220,109 B2 | 5/2007 | Kultgen |
| 7,220,236 B2 | 5/2007 | Pan |
| 7,220,365 B2 | 5/2007 | Qu et al. |
| 7,225,807 B2 | 6/2007 | Papania et al. |
| 7,226,278 B2 | 6/2007 | Nason et al. |
| 7,226,910 B2 | 6/2007 | Wilson et al. |
| 7,229,288 B2 | 6/2007 | Stuart et al. |
| 7,231,263 B2 | 6/2007 | Choi |
| 7,232,430 B2 | 6/2007 | Carlisle et al. |
| 7,232,435 B2 | 6/2007 | Hildebrand et al. |
| 7,235,164 B2 | 6/2007 | Anex et al. |
| 7,235,583 B1 | 6/2007 | Webb et al. |
| 7,238,165 B2 | 7/2007 | Vincent et al. |
| 7,239,941 B2 | 7/2007 | Möri et al. |
| 7,244,225 B2 | 7/2007 | Loeb et al. |
| 7,244,354 B2 | 7/2007 | Burris et al. |
| 7,247,428 B2 | 7/2007 | Makrigiorgos |
| 7,247,702 B2 | 7/2007 | Gardner et al. |
| 7,250,037 B2 | 7/2007 | Shermer et al. |
| 7,251,516 B2 | 7/2007 | Walker et al. |
| 7,252,014 B1 | 8/2007 | Mayer et al. |
| 7,252,651 B2 | 8/2007 | Haider et al. |
| 7,258,864 B2 | 8/2007 | Clark |
| RE39,816 E | 9/2007 | Stanton et al. |
| 7,264,730 B2 | 9/2007 | Connell et al. |
| 7,265,091 B2 | 9/2007 | Lue et al. |
| 7,267,665 B2 | 9/2007 | Steil et al. |
| 7,267,753 B2 | 9/2007 | Anex et al. |
| 7,267,771 B2 | 9/2007 | Gorsuch et al. |
| 7,268,859 B2 | 9/2007 | Sage et al. |
| 7,272,544 B2 | 9/2007 | Gopal et al. |
| 7,276,027 B2 | 10/2007 | Haar et al. |
| 7,276,028 B2 | 10/2007 | Ellingsen et al. |
| 7,276,057 B2 | 10/2007 | Gerber |
| 7,278,983 B2 | 10/2007 | Ireland et al. |
| 7,288,760 B2 | 10/2007 | Weitz |
| 7,291,133 B1 | 11/2007 | Kindler et al. |
| 7,297,151 B2 | 11/2007 | Boecker et al. |
| 7,302,295 B2 | 11/2007 | Stahmann et al. |
| 7,303,543 B1 | 12/2007 | Maule et al. |
| 7,303,549 B2 | 12/2007 | Flaherty et al. |
| 7,303,680 B2 | 12/2007 | Connell et al. |
| 7,304,033 B2 | 12/2007 | Larsen et al. |
| 7,306,555 B2 | 12/2007 | Dolecek et al. |
| 7,306,578 B2 | 12/2007 | Gray et al. |
| 7,316,700 B2 | 1/2008 | Alden et al. |
| 7,316,899 B2 | 1/2008 | McDevitt et al. |
| 7,318,892 B2 | 1/2008 | Connell et al. |
| 7,320,675 B2 | 1/2008 | Pastore et al. |
| 7,323,543 B2 | 1/2008 | Van Antwerp et al. |
| 7,324,012 B2 | 1/2008 | Mann et al. |
| 7,334,556 B2 | 2/2008 | Wachigai et al. |
| 7,338,464 B2 | 3/2008 | Blischak et al. |
| 7,341,581 B2 | 3/2008 | Mallett |
| 7,344,507 B2 | 3/2008 | Briggs et al. |
| 7,344,894 B2 | 3/2008 | Greenstein et al. |
| 7,347,201 B2 | 3/2008 | Djupesland |
| 7,347,836 B2 | 3/2008 | Peterson et al. |
| 7,348,176 B2 | 3/2008 | Dimilla et al. |
| 7,351,239 B2 | 4/2008 | Gill |
| 7,351,340 B2 | 4/2008 | Connell et al. |
| 7,351,411 B2 | 4/2008 | Holash et al. |
| 7,351,695 B2 | 4/2008 | Almarssoo et al. |
| 7,357,794 B2 | 4/2008 | Makower et al. |
| 7,357,899 B2 | 4/2008 | Gaillard et al. |
| 7,358,091 B2 | 4/2008 | Phillips et al. |
| 7,361,155 B2 | 4/2008 | Sage, Jr. et al. |
| 7,363,072 B2 | 4/2008 | Movahed |
| 7,363,075 B2 | 4/2008 | Stern et al. |
| 7,364,566 B2 | 4/2008 | Elkins et al. |
| 7,364,568 B2 | 4/2008 | Angel et al. |
| 7,366,925 B2 | 4/2008 | Keely et al. |
| 7,368,003 B2 | 5/2008 | Crapser et al. |
| 7,373,690 B2 | 5/2008 | Sepke et al. |
| 7,374,544 B2 | 5/2008 | Freeman et al. |
| 7,374,556 B2 | 5/2008 | Mallett |
| 7,378,443 B2 | 5/2008 | Berge |
| 7,380,447 B2 | 6/2008 | Rollinger et al. |
| 7,384,413 B2 | 6/2008 | Gross et al. |
| 7,384,912 B2 | 6/2008 | Stewart |
| 7,385,443 B1 | 6/2008 | Denison |
| 7,386,346 B2 | 6/2008 | Struble |
| 7,390,311 B2 | 6/2008 | Hildebrand et al. |
| 7,390,458 B2 | 6/2008 | Burow et al. |
| 7,394,182 B2 | 7/2008 | Pelrine et al. |
| 7,399,277 B2 | 7/2008 | Saidara et al. |
| 7,399,304 B2 | 7/2008 | Gambale et al. |
| 7,399,401 B2 | 7/2008 | Rush |
| 7,399,772 B2 | 7/2008 | Phillips |
| 7,402,153 B2 | 7/2008 | Steil et al. |
| 7,402,154 B2 | 7/2008 | Holst et al. |
| 7,407,489 B2 | 8/2008 | Holst et al. |
| 7,407,490 B2 | 8/2008 | Bendsen et al. |
| 7,410,468 B2 | 8/2008 | Freeman et al. |
| 7,416,644 B2 | 8/2008 | Bonde |
| 7,421,316 B2 | 9/2008 | Gray et al. |
| 7,421,882 B2 | 9/2008 | Leddy et al. |
| 7,425,204 B2 | 9/2008 | Angel et al. |
| 7,426,408 B2 | 9/2008 | Denuzzio et al. |
| 7,429,255 B2 | 9/2008 | Thompson |
| 7,429,258 B2 | 9/2008 | Angel et al. |
| 7,429,269 B2 | 9/2008 | Schwammenthal et al. |
| 7,435,250 B2 | 10/2008 | Francischelli et al. |
| 7,435,717 B2 | 10/2008 | Bisgaier et al. |
| 7,440,806 B1 | 10/2008 | Whitehurst et al. |
| 7,442,186 B2 | 10/2008 | Blomquist |
| 7,442,682 B2 | 10/2008 | Kitaura et al. |
| RE40,570 E | 11/2008 | Carpentier et al. |
| 7,446,091 B2 | 11/2008 | Van Den Berghe |
| 7,449,333 B2 | 11/2008 | Rolland et al. |
| 7,452,301 B2 | 11/2008 | Yoshioka |
| 7,455,835 B2 | 11/2008 | Cohen et al. |
| 7,462,166 B2 | 12/2008 | Cowan et al. |
| 7,463,934 B2 | 12/2008 | Tronnes et al. |
| 7,464,580 B2 | 12/2008 | Zeng et al. |
| 7,464,704 B2 | 12/2008 | Braithwaite |
| 7,465,285 B2 | 12/2008 | Hutchinson et al. |
| 7,465,375 B2 | 12/2008 | Demers et al. |
| 7,469,697 B2 | 12/2008 | Lee et al. |
| 7,469,844 B2 | 12/2008 | Conway et al. |
| 7,470,246 B2 | 12/2008 | Mori et al. |
| 7,473,247 B2 | 1/2009 | Mikszta et al. |
| 7,476,209 B2 | 1/2009 | Gara et al. |
| 7,479,123 B2 | 1/2009 | Briggs |
| 7,481,218 B2 | 1/2009 | Djupesland |
| 7,481,759 B2 | 1/2009 | Whitehurst et al. |
| 7,481,776 B2 | 1/2009 | Boecker et al. |
| 7,481,792 B2 | 1/2009 | Gonnelli et al. |
| 7,491,178 B2 | 2/2009 | Boecker et al. |
| 7,491,187 B2 | 2/2009 | Van Den Berghe et al. |
| 7,491,335 B2 | 2/2009 | Reddy et al. |
| 7,493,154 B2 | 2/2009 | Bonner et al. |
| 7,493,171 B1 | 2/2009 | Whitehurst et al. |
| 7,497,841 B2 | 3/2009 | Alchas |
| 7,503,903 B2 | 3/2009 | Carlisle et al. |
| 7,505,869 B2 | 3/2009 | Hartlaub |
| 7,507,220 B2 | 3/2009 | Childers et al. |
| 7,507,235 B2 | 3/2009 | Keogh et al. |
| 7,509,169 B2 | 3/2009 | Eigler et al. |
| 7,510,544 B2 | 3/2009 | Vilks et al. |
| 7,511,914 B2 | 3/2009 | Hiller et al. |
| 7,514,075 B2 | 4/2009 | Hedrick et al. |
| 7,515,060 B2 | 4/2009 | Blomquist |
| 7,517,335 B2 | 4/2009 | Gravesen et al. |
| 7,517,440 B2 | 4/2009 | Anex et al. |
| 7,517,498 B2 | 4/2009 | Fredrick |
| 7,517,530 B2 | 4/2009 | Clark |
| 7,524,287 B2 | 4/2009 | Bharmi |
| 7,524,293 B2 | 4/2009 | Freeman et al. |
| 7,524,304 B2 | 4/2009 | Genosar |

(56) References Cited

U.S. PATENT DOCUMENTS

| | | |
|---|---|---|
| 7,530,968 B2 | 5/2009 | Gonnelli |
| 7,530,975 B2 | 5/2009 | Hunter |
| 7,534,221 B2 | 5/2009 | Pile-Spellman |
| 7,534,226 B2 | 5/2009 | Mernoe et al. |
| 7,536,983 B2 | 5/2009 | Layher et al. |
| 7,537,571 B2 | 5/2009 | Freeman et al. |
| 7,540,880 B2 | 6/2009 | Nolting |
| 7,543,581 B2 | 6/2009 | Djupesland |
| 7,547,287 B2 | 6/2009 | Boecker et al. |
| 7,548,314 B2 | 6/2009 | Altobelli et al. |
| 7,553,813 B2 | 6/2009 | Unemori |
| 7,556,613 B2 | 7/2009 | Wittman et al. |
| 7,556,841 B2 | 7/2009 | Kimball et al. |
| 7,558,629 B2 | 7/2009 | Keimel et al. |
| 7,559,223 B2 | 7/2009 | Chen et al. |
| 7,559,524 B2 | 7/2009 | Gray et al. |
| 7,563,232 B2 | 7/2009 | Freeman et al. |
| 7,563,255 B2 | 7/2009 | Adamis et al. |
| D598,109 S | 8/2009 | Collins et al. |
| 7,571,635 B2 | 8/2009 | Lyon |
| 7,572,789 B2 | 8/2009 | Cowen et al. |
| 7,577,477 B2 | 8/2009 | Allen et al. |
| 7,582,063 B2 | 9/2009 | Wurster et al. |
| 7,582,099 B2 | 9/2009 | Freeman et al. |
| 7,584,846 B2 | 9/2009 | Senter |
| 7,588,046 B1 | 9/2009 | Erickson |
| 7,588,550 B2 | 9/2009 | Leonard et al. |
| 7,588,784 B2 | 9/2009 | Mady et al. |
| 7,589,059 B2 | 9/2009 | Wolff et al. |
| 7,590,443 B2 | 9/2009 | Bharmi et al. |
| 7,591,801 B2 | 9/2009 | Brauker et al. |
| 7,594,889 B2 | 9/2009 | St. Ores et al. |
| 7,597,682 B2 | 10/2009 | Moberg |
| 7,598,031 B2 | 10/2009 | Liew |
| 7,602,310 B2 | 10/2009 | Mann et al. |
| 7,603,174 B2 | 10/2009 | De Ridder et al. |
| 7,604,592 B2 | 10/2009 | Freeman et al. |
| 7,604,593 B2 | 10/2009 | Parris et al. |
| 7,605,710 B2 | 10/2009 | Crnkovich et al. |
| 7,606,274 B2 | 10/2009 | Mirov et al. |
| 7,606,615 B2 | 10/2009 | Makower et al. |
| 7,618,615 B2 | 11/2009 | Frey et al. |
| 7,618,954 B2 | 11/2009 | Nicolau et al. |
| 7,624,232 B2 | 11/2009 | Soejima et al. |
| 7,624,409 B2 | 11/2009 | Whymark |
| 7,625,354 B2 | 12/2009 | Hochman |
| 7,625,369 B2 | 12/2009 | Abboud et al. |
| 7,628,590 B2 | 12/2009 | Jacobsen et al. |
| 7,628,772 B2 | 12/2009 | McConnell et al. |
| 7,632,228 B2 | 12/2009 | Brauker et al. |
| 7,632,248 B2 | 12/2009 | Delk et al. |
| 7,635,575 B2 | 12/2009 | Scherze et al. |
| 7,637,279 B2 | 12/2009 | Amley et al. |
| 7,637,931 B2 | 12/2009 | Heaton |
| 7,645,253 B2 | 1/2010 | Gura |
| 7,647,107 B2 | 1/2010 | Warman |
| 7,647,115 B2 | 1/2010 | Levin et al. |
| 7,647,237 B2 | 1/2010 | Malave et al. |
| 7,650,181 B2 | 1/2010 | Freeman et al. |
| 7,650,190 B2 | 1/2010 | Zhou et al. |
| 7,651,489 B2 | 1/2010 | Estes et al. |
| 7,651,868 B2 | 1/2010 | McDevitt et al. |
| 7,653,693 B2 | 1/2010 | Heikes et al. |
| 7,654,127 B2 | 2/2010 | Krulevitch et al. |
| 7,654,131 B2 | 2/2010 | Ascheman |
| 7,654,484 B2 | 2/2010 | Mogensen et al. |
| 7,654,976 B2 | 2/2010 | Peterson et al. |
| 7,654,982 B2 | 2/2010 | Carlisle et al. |
| 7,655,221 B2 | 2/2010 | Rasmussen et al. |
| 7,657,313 B2 | 2/2010 | Rom |
| 7,662,105 B2 | 2/2010 | Hatlestad |
| 7,662,140 B2 | 2/2010 | Heruth et al. |
| 7,662,558 B2 | 2/2010 | Liew et al. |
| 7,674,243 B2 | 3/2010 | Dacquay et al. |
| 7,674,485 B2 | 3/2010 | Bhaskaran et al. |
| 7,676,263 B2 | 3/2010 | Harris |
| 7,678,071 B2 | 3/2010 | Lebel et al. |
| 7,678,762 B2 | 3/2010 | Green et al. |
| 7,678,763 B2 | 3/2010 | Green et al. |
| 7,678,772 B2 | 3/2010 | Jia et al. |
| 7,678,833 B2 | 3/2010 | Ott |
| 7,682,563 B2 | 3/2010 | Carpenter et al. |
| RE41,288 E | 4/2010 | Coolidge et al. |
| D613,411 S | 4/2010 | Collins et al. |
| 7,744,554 B2 | 6/2010 | Howard |
| 7,753,885 B2 | 7/2010 | Duchon et al. |
| 7,766,301 B2 | 8/2010 | Gray et al. |
| 7,776,006 B2 | 8/2010 | Childers et al. |
| 7,782,192 B2 | 8/2010 | Jeckelmann et al. |
| 7,790,103 B2 | 9/2010 | Shah et al. |
| 7,811,279 B2 | 10/2010 | John |
| RE41,956 E | 11/2010 | Klitgaard et al. |
| 7,831,310 B2 | 11/2010 | Lebel et al. |
| 7,837,651 B2 | 11/2010 | Bishop et al. |
| 7,867,189 B2 | 1/2011 | Childers et al. |
| 7,877,703 B1 | 1/2011 | Fleming |
| 7,905,859 B2 | 3/2011 | Bynum et al. |
| 7,912,674 B2 | 3/2011 | Killoren Clark et al. |
| 7,914,450 B2 | 3/2011 | Goode, Jr. et al. |
| 7,922,462 B2 | 4/2011 | Preuthun et al. |
| 7,935,104 B2 | 5/2011 | Yodfat et al. |
| 7,955,319 B2 | 6/2011 | Miesel |
| 7,963,945 B2 | 6/2011 | Miller et al. |
| 7,967,022 B2 | 6/2011 | Grant et al. |
| 7,972,296 B2 | 7/2011 | Braig et al. |
| 7,976,514 B2 | 7/2011 | Abry et al. |
| 7,999,927 B2 | 8/2011 | Braig et al. |
| 8,002,747 B2 | 8/2011 | Lord et al. |
| RE42,682 E | 9/2011 | Barreras, Sr. et al. |
| 8,029,454 B2 | 10/2011 | Kelly et al. |
| 8,030,058 B1 | 10/2011 | Benedict et al. |
| 8,032,226 B2 | 10/2011 | Miller et al. |
| 8,043,281 B2 | 10/2011 | Heruth et al. |
| RE42,958 E | 11/2011 | Loeb et al. |
| 8,056,582 B2 | 11/2011 | DiPerna |
| 8,062,257 B2 | 11/2011 | Moberg et al. |
| 8,065,096 B2 | 11/2011 | Moberg et al. |
| 8,065,161 B2 | 11/2011 | Howard et al. |
| 8,066,629 B2 | 11/2011 | Dlugos |
| 8,078,983 B2 | 12/2011 | Davis et al. |
| 8,094,009 B2 | 1/2012 | Allen et al. |
| 8,096,487 B2 | 1/2012 | Hornsby |
| 8,100,842 B2 | 1/2012 | Rousso |
| 8,105,265 B2 | 1/2012 | Demers et al. |
| 8,130,095 B2 | 3/2012 | Allen et al. |
| 8,147,451 B2 | 4/2012 | Brockman et al. |
| 8,149,131 B2 | 4/2012 | Blomquist |
| 8,152,764 B2 | 4/2012 | Istoc et al. |
| 8,177,739 B2 | 5/2012 | Cartledge et al. |
| 8,182,447 B2 | 5/2012 | Moberg et al. |
| 8,182,461 B2 | 5/2012 | Pope et al. |
| 8,182,462 B2 | 5/2012 | Istoc et al. |
| 8,187,228 B2 | 5/2012 | Bikovsky |
| 8,192,394 B2 | 6/2012 | Estes et al. |
| 8,206,350 B2 | 6/2012 | Mann et al. |
| 8,211,062 B2 | 7/2012 | Estes et al. |
| 8,211,093 B2 | 7/2012 | Miller et al. |
| 8,211,364 B2 | 7/2012 | Drucker et al. |
| 8,231,562 B2 | 7/2012 | Buck et al. |
| 8,231,572 B2 | 7/2012 | Carter et al. |
| 8,231,578 B2 | 7/2012 | Fathallah et al. |
| 8,234,126 B1 | 7/2012 | Estes |
| 8,234,128 B2 | 7/2012 | Martucci et al. |
| 8,237,715 B2 | 8/2012 | Buck et al. |
| 8,251,906 B2 | 8/2012 | Brauker et al. |
| 8,257,259 B2 | 9/2012 | Brauker et al. |
| 8,257,652 B2 | 9/2012 | Drucker et al. |
| 8,257,653 B2 | 9/2012 | Drucker et al. |
| 8,267,893 B2 | 9/2012 | Moberg et al. |
| 8,285,328 B2 | 10/2012 | Caffey et al. |
| 8,287,454 B2 | 10/2012 | Wolpert et al. |
| 8,287,495 B2 | 10/2012 | Michaud et al. |
| 8,287,521 B2 | 10/2012 | Kriesel et al. |
| 8,292,876 B2 | 10/2012 | Kriesel et al. |

(56) References Cited

U.S. PATENT DOCUMENTS

| | | |
|---|---|---|
| 8,298,183 B2 | 10/2012 | Menot et al. |
| 8,298,184 B2 | 10/2012 | DiPerna et al. |
| 8,317,752 B2 | 11/2012 | Cozmi et al. |
| 8,328,754 B2 | 12/2012 | Estes et al. |
| 8,328,793 B2 | 12/2012 | Birkenbach et al. |
| 8,344,847 B2 | 1/2013 | Moberg et al. |
| 8,348,886 B2 | 1/2013 | Kanderian et al. |
| 8,348,923 B2 | 1/2013 | Kanderian et al. |
| 8,361,030 B2 | 1/2013 | Carter |
| 8,372,040 B2 | 2/2013 | Huang et al. |
| 8,376,943 B2 | 2/2013 | Kovach et al. |
| 8,380,536 B2 | 2/2013 | Howard et al. |
| 8,395,581 B2 | 3/2013 | Graskov |
| 8,398,592 B2 | 3/2013 | Leibner-Druska |
| 8,407,063 B2 | 3/2013 | Brown |
| 8,408,421 B2 | 4/2013 | DiPerna |
| 8,414,557 B2 | 4/2013 | Istoc et al. |
| 8,414,563 B2 | 4/2013 | Kamen |
| 8,435,206 B2 | 5/2013 | Evans et al. |
| 8,444,592 B2 | 5/2013 | Williams et al. |
| 8,449,524 B2 | 5/2013 | Braig et al. |
| 8,452,953 B2 | 5/2013 | Buck et al. |
| 8,454,562 B1 | 6/2013 | Sims |
| 8,454,575 B2 | 6/2013 | Estes et al. |
| 8,524,154 B2 | 9/2013 | Shekalim et al. |
| 8,573,027 B2 | 11/2013 | Rosinko et al. |
| 8,641,671 B2 | 2/2014 | Michaud et al. |
| 8,758,323 B2 | 6/2014 | Michaud et al. |
| 8,926,561 B2 | 1/2015 | Verhoef et al. |
| 8,986,253 B2 | 3/2015 | DiPerna |
| 2001/0027791 A1 | 10/2001 | Wallace et al. |
| 2002/0019714 A1 | 2/2002 | Carliale et al. |
| 2002/0040208 A1 | 4/2002 | Flaherty et al. |
| 2002/0045265 A1 | 4/2002 | Bergh et al. |
| 2002/0048536 A1 | 4/2002 | Bergh et al. |
| 2002/0072733 A1 | 6/2002 | Flaherty |
| 2003/0032930 A1 | 2/2003 | Branch et al. |
| 2003/0060765 A1 | 3/2003 | Campbell et al. |
| 2003/0065287 A1 | 4/2003 | Spohn et al. |
| 2003/0199378 A1 | 10/2003 | Saviano |
| 2003/0216683 A1 | 11/2003 | Shekalim |
| 2004/0122353 A1 | 6/2004 | Shahmirian et al. |
| 2004/0204673 A1 | 10/2004 | Flaherty |
| 2004/0260233 A1 | 12/2004 | Garibotto et al. |
| 2005/0004514 A1 | 1/2005 | Hochman |
| 2005/0020980 A1 | 1/2005 | Inoue et al. |
| 2005/0137578 A1 | 6/2005 | Heruth et al. |
| 2005/0171512 A1 | 8/2005 | Flaherty |
| 2006/0147313 A1 | 7/2006 | Zengerle et al. |
| 2006/0150747 A1 | 7/2006 | Mallett |
| 2006/0150748 A1 | 7/2006 | Mallett |
| 2006/0206054 A1 | 9/2006 | Shekalim |
| 2006/0229557 A1 | 10/2006 | Fathallah et al. |
| 2006/0264835 A1 | 11/2006 | Nielsen et al. |
| 2006/0271022 A1 | 11/2006 | Steinbach et al. |
| 2007/0003434 A1 | 1/2007 | Padmanabhan et al. |
| 2007/0033074 A1 | 2/2007 | Nitzan et al. |
| 2007/0112301 A1 | 5/2007 | Preuthun et al. |
| 2007/0118405 A1 | 5/2007 | Campbell et al. |
| 2007/0149926 A1 | 6/2007 | Moberg et al. |
| 2007/0161955 A1 | 7/2007 | Bynum et al. |
| 2007/0219496 A1 | 9/2007 | Kamen et al. |
| 2007/0250007 A1 | 10/2007 | Shekalim |
| 2007/0264130 A1 | 11/2007 | Mallett |
| 2007/0287985 A1 | 12/2007 | Estes et al. |
| 2007/0288176 A1 | 12/2007 | Carlisle et al. |
| 2008/0029173 A1 | 2/2008 | DiPerna |
| 2008/0033357 A1 | 2/2008 | Mann et al. |
| 2008/0051716 A1 | 3/2008 | Stutz |
| 2008/0058697 A1 | 3/2008 | Kamen et al. |
| 2008/0065007 A1 | 3/2008 | Peterson et al. |
| 2008/0065016 A1 | 3/2008 | Peterson et al. |
| 2008/0071220 A1 | 3/2008 | Rhinehart et al. |
| 2008/0092969 A1 | 4/2008 | DiPerna |
| 2008/0097375 A1 | 4/2008 | Bikovsky |
| 2008/0114228 A1 | 5/2008 | McCluskey et al. |
| 2008/0116647 A1 | 5/2008 | Anderson et al. |
| 2008/0147004 A1 | 6/2008 | Mann et al. |
| 2008/0147050 A1 | 6/2008 | Mann et al. |
| 2008/0160492 A1 | 7/2008 | Campbell et al. |
| 2008/0196762 A1 | 8/2008 | Mallett |
| 2008/0197801 A1 | 8/2008 | Manor et al. |
| 2008/0234637 A1 | 9/2008 | McConnell et al. |
| 2008/0269584 A1 | 10/2008 | Shekalim et al. |
| 2009/0026146 A1 | 1/2009 | Carlisle et al. |
| 2009/0069785 A1 | 3/2009 | Miller et al. |
| 2009/0131863 A1 | 5/2009 | Carlisle et al. |
| 2009/0191067 A1 | 7/2009 | DiPerna |
| 2009/0192366 A1 | 7/2009 | Mensinger |
| 2009/0192724 A1 | 7/2009 | Brauker et al. |
| 2009/0192745 A1 | 7/2009 | Kamath |
| 2009/0217982 A1 | 9/2009 | DiPerna |
| 2009/0227888 A1 | 9/2009 | Salmi et al. |
| 2009/0229374 A1 | 9/2009 | Carlisle et al. |
| 2009/0234594 A1 | 9/2009 | Carlisle et al. |
| 2009/0240193 A1 | 9/2009 | Mensinger et al. |
| 2009/0254037 A1 | 10/2009 | Bryant et al. |
| 2009/0270833 A1 | 10/2009 | DeBelser et al. |
| 2009/0275896 A1 | 11/2009 | Kamen et al. |
| 2009/0287180 A1 | 11/2009 | DiPerna |
| 2009/0289916 A1 | 11/2009 | Dai |
| 2010/0008795 A1 | 1/2010 | DiPerna |
| 2010/0028208 A1 | 2/2010 | Shekalim et al. |
| 2010/0032041 A1 | 2/2010 | DiPerna |
| 2010/0036327 A1 | 2/2010 | DiPerna |
| 2010/0063765 A1 | 3/2010 | Carlisle et al. |
| 2010/0065578 A1 | 3/2010 | DiPerna |
| 2010/0065579 A1 | 3/2010 | DiPerna |
| 2010/0094114 A1 | 4/2010 | Robinson et al. |
| 2010/0096019 A1 | 4/2010 | DiPerna |
| 2010/0121306 A1 | 5/2010 | Yodfat et al. |
| 2010/0168543 A1 | 7/2010 | Kamath et al. |
| 2010/0179402 A1 | 7/2010 | Goode, Jr. et al. |
| 2010/0185142 A1 | 7/2010 | Kamen et al. |
| 2010/0185175 A1 | 7/2010 | Kamen et al. |
| 2010/0192686 A1 | 8/2010 | Kamen et al. |
| 2010/0198183 A1 | 8/2010 | Lanigan et al. |
| 2010/0218586 A1 | 9/2010 | Rosinko et al. |
| 2010/0253768 A1 | 10/2010 | El-Maraghi et al. |
| 2010/0256466 A1 | 10/2010 | Shekalim et al. |
| 2010/0274515 A1 | 10/2010 | Hoss et al. |
| 2010/0298681 A1 | 11/2010 | Say |
| 2010/0324394 A1 | 12/2010 | Say et al. |
| 2011/0004188 A1 | 1/2011 | Shekalim et al. |
| 2011/0009798 A1 | 1/2011 | Kelly et al. |
| 2011/0009813 A1 | 1/2011 | Rankers |
| 2011/0028937 A1 | 2/2011 | Powers et al. |
| 2011/0056264 A1 | 3/2011 | Kaplan et al. |
| 2011/0060280 A1 | 3/2011 | Caffey et al. |
| 2011/0108158 A1 | 5/2011 | Huwiler et al. |
| 2011/0120206 A1 | 5/2011 | Troughton et al. |
| 2011/0144586 A1 | 6/2011 | Michaud et al. |
| 2011/0144616 A1 | 6/2011 | Michaud et al. |
| 2011/0152653 A1 | 6/2011 | Shekalim et al. |
| 2011/0152770 A1 | 6/2011 | DiPerna |
| 2011/0152824 A1 | 6/2011 | DiPerna et al. |
| 2011/0160654 A1 | 6/2011 | Hanson et al. |
| 2011/0163125 A1 | 7/2011 | Beavis et al. |
| 2011/0166544 A1 | 7/2011 | Verhoef et al. |
| 2011/0190694 A1 | 8/2011 | Lanier, Jr. et al. |
| 2011/0309107 A1 | 12/2011 | Shekalim et al. |
| 2011/0319862 A1 | 12/2011 | Friedman et al. |
| 2012/0029433 A1 | 2/2012 | Michaud et al. |
| 2012/0029468 A1* | 2/2012 | Diperna ............ A61M 5/1413 604/500 |
| 2012/0029486 A1 | 2/2012 | Laerdal et al. |
| 2012/0029708 A1 | 2/2012 | Miller et al. |
| 2012/0030610 A1 | 2/2012 | DiPerna et al. |
| 2012/0041415 A1 | 2/2012 | Estes et al. |
| 2012/0059673 A1 | 3/2012 | Cohen et al. |
| 2012/0232520 A1 | 9/2012 | Sloan et al. |
| 2013/0012877 A1 | 1/2013 | Debelser et al. |
| 2013/0053816 A1 | 2/2013 | DiPerna et al. |
| 2013/0150766 A1 | 6/2013 | Olde et al. |

(56) References Cited

U.S. PATENT DOCUMENTS

| | | |
|---|---|---|
| 2013/0204542 A1 | 8/2013 | Olde et al. |
| 2013/0283196 A1 | 10/2013 | Farnan et al. |
| 2013/0298024 A1 | 11/2013 | Rhee et al. |
| 2013/0306191 A1 | 11/2013 | Metzmaker et al. |
| 2013/0324928 A1 | 12/2013 | Kruse |
| 2013/0332874 A1 | 12/2013 | Rosinko et al. |
| 2014/0039805 A1 | 2/2014 | Sharpe, Jr. et al. |
| 2014/0054883 A1 | 2/2014 | Lanigan et al. |
| 2014/0094764 A1 | 4/2014 | Blomquist et al. |
| 2014/0276538 A1 | 9/2014 | Michaud |

FOREIGN PATENT DOCUMENTS

| | | |
|---|---|---|
| KR | 1020010080519 | 8/2001 |
| WO | WO9532013 | 11/1995 |
| WO | WO9608040 | 3/1996 |
| WO | WO9613288 | 5/1996 |
| WO | WO9625189 | 8/1996 |
| WO | WO9857683 | 12/1998 |
| WO | WO9901088 | 1/1999 |
| WO | WO0072900 | 12/2000 |
| WO | WO0130422 | 5/2001 |
| WO | WO2004009160 | 1/2004 |
| WO | WO2005082450 | 9/2005 |
| WO | WO2007/065944 | 6/2007 |
| WO | WO2007065944 A1 | 6/2007 |
| WO | WO2007119149 | 10/2007 |
| WO | WO2008/024812 | 2/2008 |
| WO | WO2008037272 | 4/2008 |
| WO | WO2009/016636 | 2/2009 |
| WO | WO2009044221 | 4/2009 |
| WO | WO2009094590 | 7/2009 |
| WO | WO2009108639 | 9/2009 |
| WO | WO2009143188 | 11/2009 |
| WO | WO2012019726 | 2/2012 |

OTHER PUBLICATIONS

International Search Report and Written Opinion for International Application No. PCT/US2007/060633 dated Jul. 23, 2007.
International Search Report and Written Opinion for International Application No. PCT/US2009/049110 dated Jan. 27, 2010.
International Search Report and Written Opinion for International Application No. PCT/US2009/09116 dated Feb. 4, 2010.
International Search Report and Written Opinion for International Application No. PCT/US2009/031906 dated Jul. 28, 2009.
International Search Report and Written Opinion for International Application No. PCT/US2009/044569 dated Jan. 4, 2010.
International Search Report and Written Opinion for International Application No. PCT/US2010/043789 dated Apr. 11, 2011.
Application and File History for U.S. Appl. No. 12/846,734, filed Jul. 29, 2010, inventors Verhoef et al.
Application and File History for U.S. Appl. No. 13/270,160, filed Oct. 10, 2011 inventors Michaud et al.
Application and File History for U.S. Appl. No. 13/271,156, filed Oct. 11, 2011 inventors DiPerna et al.
Application and File History for U.S. Appl. No. 13/273,484, filed Oct. 14, 2011 inventors DiPerna et al.
Application and File History for U.S. Appl. No. 13/842,990, filed Mar. 15, 2013, inventors Michaud.
Application and File History for U.S. Appl. No. 12/468,795, filed May 19, 2009, inventor DiPerna.
International Search Report and Written Opinion for International Application No. PCT/US2013/044259 dated Sep. 6, 2013.
European Search Report for European Application No. EP10805076 dated Mar. 18, 2013.
European Search Report for European Application No. EP09704892 dated Jan. 28, 2013.
European Search Report for European Application No. EP09751416.0-2319 dated Nov. 21, 2012.
Examination Report No. 1 for Australian Patent Application No. 2009249132 dated Jan. 23, 2014.
European Search Report for European Application No. 14152623.6-1506 dated Mar. 11, 2014.
Application and File History for U.S. Appl. No. 12/020,498, filed Jan. 25, 2008, inventor DiPerna.
Application and File History for U.S. Appl. No. 12/538,018, filed Aug. 7, 2009, inventor DiPerna.
I-port Advance Product brochure distributed by: Patton Medical Devices and Manufactured by Unomedical, a Cardiovascular Company, Copy right 2007-2010. Patton Medical Devices, LP.
Arrow International Europe Webpage for: Multiple Lumen Peripheral Catheter, Product No, IV-01150, printed from the internet on Nov. 15, 2011.
AngioDynamics, Smart Port, Power-Injectable Ports Product Brochure, Copyright 2010. Angio Dynamics, Inc.
Spring Zone Insulin Delivery System Product Brochure, Copyright 2011. Spring (formerly NiliMEDIX),a D-Medical Company.
Miller, John E., "The Reciprocating Pump, Theory, Design and Use," Chapter 1, "Pump Types", Krieger Publishing Company. Malabar, FL 1995.
Application and File History for U.S. Appl. No. 12/846,688, filed Jul. 29, 2010, inventors DiPerna et al.
International Search Report and Written Opinion for International Application No. PCT/US2014/021171 dated Jun. 8, 2014.
Canadian Examiner's Report for Canadian Application No. 2,769,030 dated Aug. 27, 2014.
Application and File History for U.S. Appl. No. 12/846,706, filed Jul. 29, 2010, inventors Michaud et al.
Application and File History for U.S. Appl. No. 12/846,720, filed Jul. 29, 2010, inventors DiPerna et al.
Application and File History for U.S. Appl. No. 12/846,733, filed Jul. 29, 2010, inventors Michaud et al.
European Search Report mailed Mar. 3, 2016 (dated Feb. 23, 2016 for European Application No. 13800986.5.

\* cited by examiner

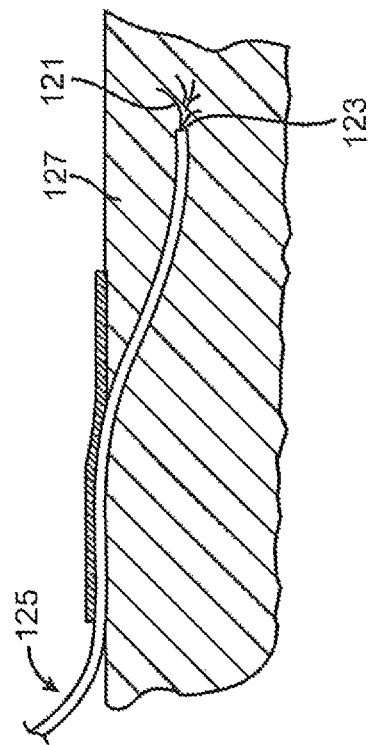
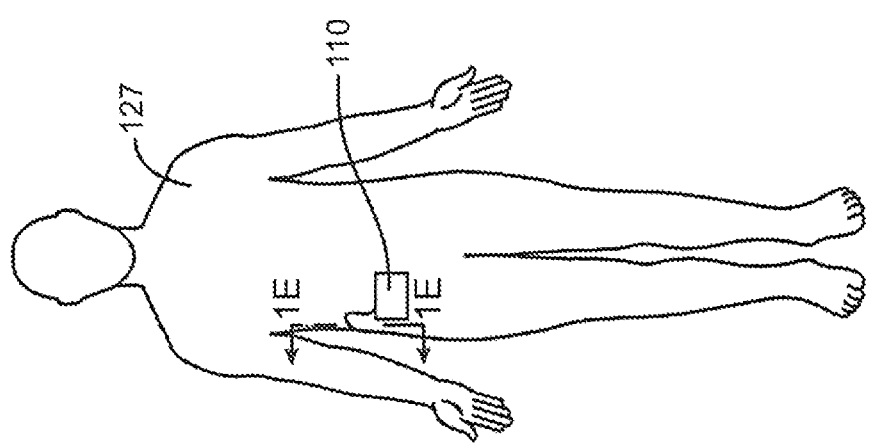

INFUSION PUMP SYSTEM WITH DISPOSABLE CARTRIDGE HAVING PRESSURE VENTING AND PRESSURE FEEDBACK

RELATED APPLICATION

The present application claims the benefit of U.S. Provisional Application No. 61/655,883 filed Jun. 5, 2012, which is incorporated herein in its entirety by reference.

FIELD OF THE INVENTION

This disclosure is directed to portable infusion devices, systems, and methods of using the same for dispensing materials. In some cases, the devices, systems and methods may be used for infusing a material such as medicament, e.g., insulin, into a body in need thereof.

BACKGROUND

There are many applications in academic, industrial, and medical fields, as well as others, that benefit from devices and methods that are capable of accurately and controllably delivering fluids, including liquids and gases that have a beneficial effect when administered in known and controlled quantities. This is particularly true in the medical field where treatments for many patients include the administration of a known amount of a substance at predetermined intervals. The treatment of diabetes involves just such a regimented dosage medicaments such as insulin. In addition, the administration of insulin for a diabetic patient is one of a few medical indications wherein patients routinely administer the medicament to themselves by a subcutaneous modality, such as a hypodermic syringe injection. As such, providing a patient with the means to safely, reliably and comfortably administer required doses of medication may be particularly important in order to facilitate patient compliance and accurate treatment of the condition.

Continuous subcutaneous insulin injection and/or infusion therapy is initiated for the replacement of insulin and thereby the treatment of diabetes. Such therapy may include the regular and/or continuous injection or infusion of insulin into the skin of a person suffering from diabetes, injection is the traditional method for administering insulin. Typically the diabetic will measure his or her blood glucose level and depending on the level thereof may prepare a syringe or injection pen with insulin to be injected transdermally into the body. However, insulin injecting pumps have also been developed for the administration of insulin for those suffering from both type I and II diabetes. Insulin pumps are medical devices used for the administration of insulin in the treatment of diabetes and offer an alternative to multiple daily injections of insulin by an insulin syringe or an insulin pen. They also allow for continuous insulin therapy. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. Provisional Patent Application No. 61/656,967 and U.S. Pat. No. 8,287,495, each of which is incorporated herein by reference.

SUMMARY

Systems and methods of venting a cartridge of an infusion pump system are disclosed. The system can be actively or passively vented. A interior volume of the system can be actively vented at times when a drive mechanism of the system is inactive. Such an active venting system can include a valve that seals a cartridge of the system from the interior volume and ambient when pressure measurements in the cartridge are made by a pressure sensor for greater measurement and calculation accuracy. In a passive venting system, a passageway that can be formed by micro-capillary tubing provides a controlled, predictable venting of the interior volume.

In some embodiments, an infusion pump system includes a pump device, a fluid cartridge with a delivery mechanism, a pressure sensor, a bore within a pump body of the delivery mechanism, and a spool slidingly disposed in the bore. The pump device may include a housing, a drive mechanism with a motor, a controller operatively coupled to the drive mechanism, and a slot configured to accept the fluid cartridge. The fluid cartridge may be operatively coupled to the housing, the cartridge including a delivery mechanism, a collapsible reservoir having an interior volume surrounded by a flexible fluid tight membrane, the interior volume being in fluid communication with a reservoir inlet port, the cartridge also including a substantially rigid shell disposed over the reservoir and forming a second interior volume between an outside surface of the reservoir and an inside surface of the rigid shell with a vent inlet port in communication with the second interior volume. The fluid cartridge can include a valve which selectively closes the vent inlet port. A pressure sensor can be disposed between an interior surface of the rigid ease and an exterior surface of the collapsible reservoir.

The following additional features may be included in embodiments of an infusion pump system in any suitable combination. The system may be such that at least one seal is always disposed between the reservoir inlet port and dispense port so as to prevent a free flow condition to the dispense port from the reservoir in some embodiments. The collapsible first volume may be formed between two seals disposed on the spool body, an inside surface of the bore, and an outside of the spool body disposed between the two seals with the seals axially displaceable relative to each other to form a collapsible volume between the two seals. The pressure sensor of the system may be configured to measure small changes in pressure at low pressures. In some such embodiments, the pressure sensor may be configured to measure pressures up to about 30 psi. The pressure sensor may be configured to measure pressures up to about 5 psi in some such embodiments. In some embodiments, the seals of the spool may include o-rings disposed in angled grooves having overflow grooves below and in communication with the angled grooves. The collapsible first volume my include a section of the spool disposed between the seals of the collapsible first volume that is axially collapsible to allow the seals of the collapsible first volume to axially converge and reduce the volume of the collapsible first volume in some embodiments.

Some embodiments are directed to an infusion pump system that includes a pump device and a fluid cartridge. The pump device of such embodiments may include a housing, a drive mechanism with a motor, a controller operatively coupled to the drive mechanism, and a slot configured to accept a fluid cartridge. Such embodiments may also include a fluid cartridge that may be operatively coupled to the housing, the cartridge including a delivery mechanism, a collapsible reservoir having an interior volume surrounded by a flexible fluid tight membrane, the interior volume being in fluid communication with a reservoir inlet port, the cartridge also including a substantially rigid shell disposed over the reservoir and forming a second interior volume between an outside surface of the reservoir and an inside surface of the rigid shell. The infusion pump system may, in some embodiments, further include a passageway that fluidly connects the second interior volume of the cartridge with an ambient environment outside of the fluid cartridge, such that pressure within the second interior volume equilibrates with ambient pressure after a predetermined time period. In some embodiments, the infusion pump system may further include a pressure sensor disposed between an interior surface of the rigid case and an exterior surface of the collapsible reservoir shell a bore within a pump body of the delivery mechanism, and a spool slidingly disposed in the bore having a collapsible first volume that is configured to communicate with the reservoir inlet port and dispense port of the bore independently of each other.

The following additional features may be included in embodiments of an infusion pump system in any suitable combination. In some embodiments, the predetermined time period for equilibration may be at least 30 seconds. The predetermine time period for equilibration may be between about 30 and about 60 seconds in some embodiments.

In such embodiments, the method includes initiating a dispense cycle of an infusion pump system, executing the dispense cycle, repeating the dispense cycle until a desired amount of fluid is dispensed, and driving the spool of the infusion pump system to a position with the vent second volume in simultaneous communication with the vent inlet port and vent outlet port after the desired amount of fluid is dispensed. The infusion pump system of such embodiments may include a fluid reservoir cartridge with a delivery mechanism, a collapsible fluid reservoir, and a substantially rigid shell disposed about the collapsible fluid reservoir with an interior volume that contains the collapsible fluid reservoir and a interior volume disposed between an outer surface of the flexible membrane and an interior surface of the rigid shell, the vent inlet port being in fluid communication with the interior volume. The infusion pump system may also include a drive mechanism operatively coupled to the delivery system. The delivery mechanism of the infusion pump system may include a delivery mechanism body and a bore disposed in the delivery mechanism body that includes a distal end, a proximal end disposed towards a drive mechanism of the infusion pump, an interior volume, a reservoir inlet port, a fluid dispense port, a vent inlet port, and a vent outlet port. A spool that is slidingly disposed within the bore may be part of the delivery mechanism. The spool may include a collapsible first volume which is positionable to overlap the reservoir inlet port independent of an overlap of the fluid dispense port and which is formed between a first seal around the spool, a second seal around the spool, an outer surface of the spool body between the first and second seal and an interior surface of the bore between the first and second seal, the first and second seals being axially moveable relative to each other. The spool may further include a vent second volume which is positionable to overlap the vent inlet port and vent outlet port simultaneously and which is formed by a third seal around the spool, a fourth seal around the spool, an outside surface of the spool between the third and fourth seal, and an inside surface of the bore between the third and fourth seal. The drive mechanism may be operatively coupled to the spool of the delivery mechanism. In some embodiments, the dispense cycle includes driving the spool with the drive mechanism to a position with the collapsible first volume in communication with the reservoir inlet port, driving the spools as to separate the first and second seals of the collapsible first volume and draw fluid into the first volume through the reservoir inlet port from the reservoir and decrease the pressure within the interior volume, driving the spool with the drive mechanism to a position with the collapsible first volume in communication with the fluid dispense port, and driving the spool so as to at least partially collapse the collapsible first volume and dispense fluid from the collapsible first volume through the fluid dispense port. In some embodiments the vent second volume is in simultaneous communication with the vent inlet port and vent outlet port after every dispense cycle.

The following additional features may be included in embodiments of a method of venting a cartridge of an infusion pump system in any suitable combination. The vent second volume is moved to no longer communicate with the vent inlet port and vent outlet port before the dispense cycle is executed in some embodiments. In some embodiments, a first and second pressure measurement is taken to reflect the pressure in the interior volume before and after the desired amount of fluid is dispensed while the vent second volume is not in communication with the vent inlet port and vent outlet port.

Some embodiments are directed to a method of venting a cartridge of an infusion pump system, in which the method includes initiating a dispense cycle of an infusion pump system, executing the dispense cycle, and repealing the dispense cycle until a desired amount of fluid is dispensed. In such embodiments, the infusion pump system may include a fluid reservoir cartridge that includes a delivery mechanism, a collapsible fluid reservoir bounded by a flexible membrane and including an interior volume in fluid communication with the reservoir inlet port, a substantially rigid shell disposed about the collapsible fluid reservoir, a passive venting mechanism, and a drive mechanism. Further, in such embodiments, the rigid shell disposed about the collapsible fluid reservoir may also include a interior volume disposed between an outer surface of the flexible membrane and an interior surface of the rigid shell, and the vent inlet port may be in fluid communication with the interior volume. The passive venting mechanism may fluidly communicate between the interior volume and the exterior of substantially rigid shell such that during periods immediately after execution of a dispense cycle, pressure in the interior volume is not equal to pressure outside the rigid shell. The dispense cycle may include driving the spool with the drive mechanism to a position with the collapsible first volume in communication with the reservoir inlet port, driving the spool so as to separate the first and second seals of the collapsible first volume and draw fluid into the first volume through the reservoir inlet port from the reservoir and decrease the pressure within the interior volume, driving the spool with the drive mechanism to a position with the collapsible first volume in communication with the fluid dispense port, and driving the spool so as to at least partially collapse the collapsible first volume and dispense fluid from the collapsible first volume through the fluid dispense port. In some such embodiments, the delivery mechanism may include a delivery mechanism body, a bore disposed in the delivery mechanism body, and a spool slidingly disposed within the bore. The bore may include a distal end, a proximal end disposed towards a drive mechanism of the infusion pump, an interior volume, a reservoir inlet port, a fluid dispense port, a vent inlet port, and a vent outlet port. The spool may include a collapsible first volume and a vent second volume. The first volume of the spool may be positionable to overlap the reservoir inlet port independent of an overlap of the fluid dispense port and may be formed between a first seat around the spool, a second seal around the spool, an outer surface of the spool body between the first and second seal, and an interior surface of the bore between the first and second seal, the first and second seals being axially moveable relative to each other. The vent second volume may be positionable to overlap the vent inlet port and vent outlet port simultaneously and may be formed by a third seal around the spoof a fourth seal around the spool, an outside surface of the spool between the third and fourth seal and an inside surface of the bore between the third and fourth seal.

The following additional features may be included in embodiments of a method of venting a cartridge of an infusion pump system in any suitable combination. In some embodiments, the method may further include driving the spool to a position with the vent second volume in simultaneous communication with the vent inlet port and vent outlet port after the desired amount of fluid is dispensed when a pressure difference between the pressure in the interior volume varies from pressure outside the rigid shell by more than a threshold value. The threshold value in such embodiments may be 0.5 psi gauge. Alternatively, the threshold value in such embodiments may be 0.25 psi gauge.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

FIG. 1D depicts an embodiment of an infusion pump system in operative communication with a patient.

FIG. 1E depicts an enlarged view in partial section of a distal end of an infusion line of the infusion pump system of FIG. 1D disposed subcutaneously in the patient.

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

Provided herein are systems, devices and methods for venting a cartridge of an infusion pump system. Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments, including, for example, glucagon and pramlintide, as well as other applications are also contemplated. Device and method embodiments discussed herein may be used for pain medication, chemotherapy, iron chelation, immunoglobulin treatment, dextrose or saline IV delivery, or any other suitable indication or application. Non-medical applications are also contemplated.

Figure 1A:
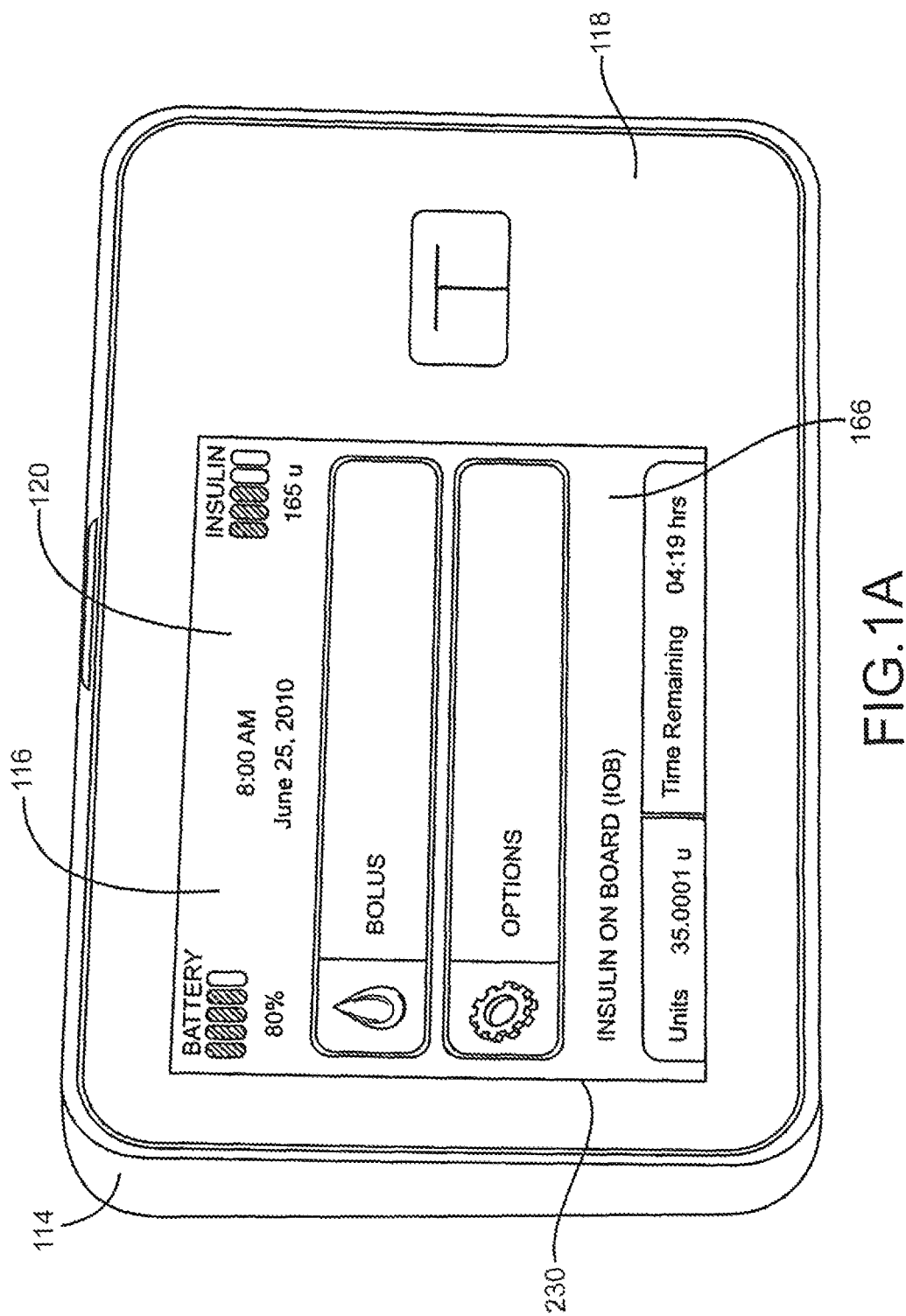
FIG. 1A is a front view in perspective of an embodiment of an infusion pump according to an embodiment of the present invention.
Figure 1B:
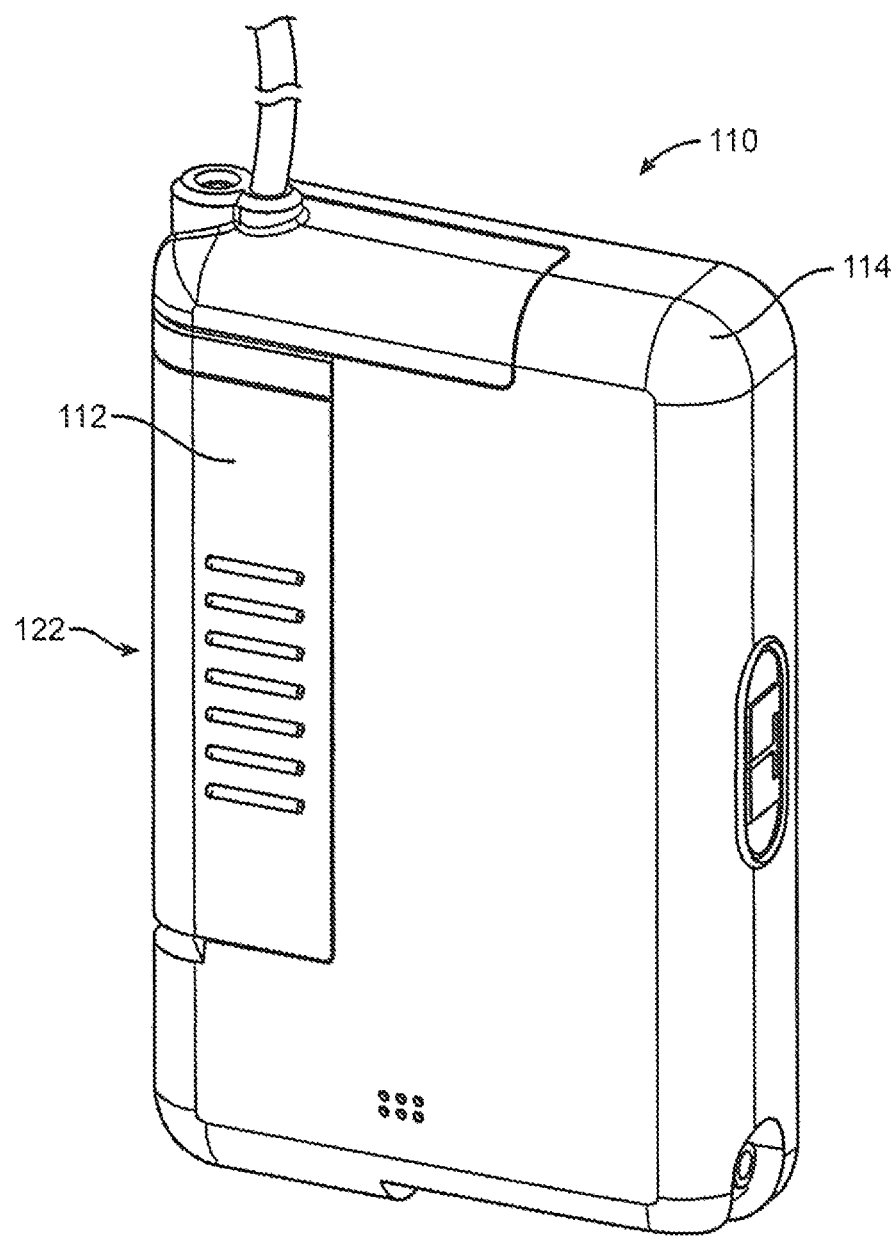
FIG. 1B is a rear view of an infusion cartridge coupled to the infusion pump of FIG. 1A.

FIGS. 1A-3 show an infusion pump system 110 including an infusion cartridge 112 and pump device 114 according to an embodiment of the present invention. In some embodiments, the infusion cartridge 112 is a reversibly removable and Interchangeable element that may be inserted into different pump devices. Referring to FIG. 1A, a front view of the pump device 114 is shown and includes a user friendly user interface 116 on a front surface 118 of the pump device 114. The user interface 116 can include a touch sensitive screen 120 that may be configured to display a variety of screens used for displaying data, facilitating data entry by a patient, providing visual tutorials, as well as other interface features that may be useful to a patient operating the pump device 114. FIG. 1B is a rear view of the pump device 114 and illustrates the detachable installment of the infusion cartridge 112 in a slot 122 of the pump device 114 which is configured to accept the cartridge 112.

Figure 1C:
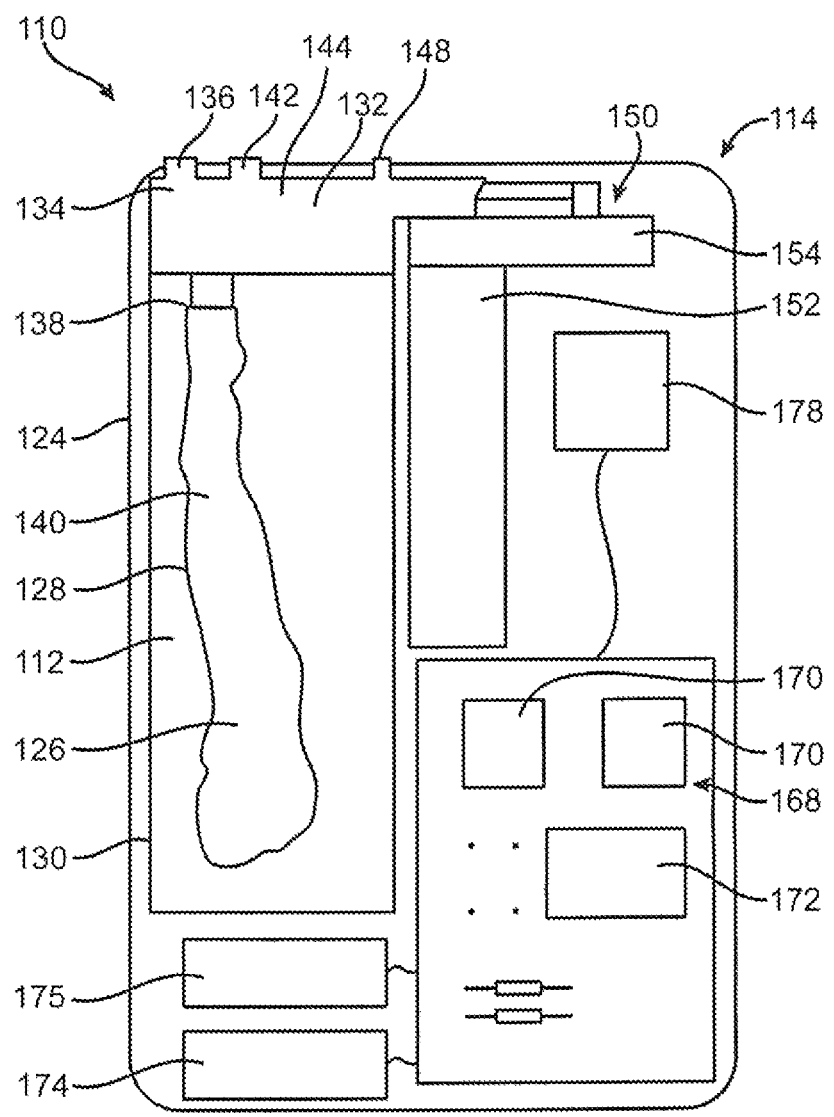
FIG. 1C is a rear schematic view of an interior of the infusion pump and cartridge embodiments of FIG. 1A.

FIG. 1C is a schematic view of an open housing 124 of the pump device 114 which shows schematically some components that may be included in embodiments of the pump device 114. FIG. 1D shows the pump system 110 operatively coupled to a patient 127. FIG. 1E shows an outlet 123 of an infusion set 125 disposed beneath the skin of a patient 127. The infusion set is in fluid communication with a dispense part at the pump system 110 and a fluid 121, such as insulin or other suitable medicament, is shown being disposed form the outlet 123 into the body of the patient 127.

For some embodiments, the pump system 110 may include a disposable fluid reservoir cartridge 112. The disposable cartridge 112 may include a fluid interface configured to receive a fluid such as collapsible reservoir 126. The collapsible reservoir 126 may be formed from a flexible material or membrane 128 that is disposed about an interior volume of the reservoir 126. The cartridge 112 also includes a substantially rigid container 130 sealed around the flexible material of the collapsible reservoir 126. A disposable delivery mechanism 132 is disposed within the disposable cartridge 112 and may have a fill port 134 with a re-sealable septum 136 sealed over the fill port 134, a reservoir inlet port 138 in fluid communication with an interior volume 140 of the collapsible reservoir 126, a fluid dispense port 142 in fluid communication with a bore 144 of the delivery mechanism 132, a vent inlet port 146 and a vent outlet port 148 both in fluid communication with the bore 144. The collapsible reservoir 126 may have a bag-like structure with flexible walls that can collapse and expand depending upon the amount of material in the volume of the reservoir. The interior volume of the reservoir may be in fluid isolation from the remaining interior volume of the rigid container 130.

The cartridge 112 may be releasably and operatively secured to a housing 124 of the pump device 114. The housing 124 may be configured to house a drive mechanism 150 including a motor 152 and gear box 154 disposed in the housing 124 and detachably coupled to a spool member 156 of the delivery mechanism 132. The drive mechanism 150 may be detachably and operatively coupled to the spool 156 member of the delivery mechanism 132. At least one pressure sensor 158 may be disposed in a volume 160 between an outside surface 162 of the flexible material or membrane 128 of the collapsible reservoir 126 and an inside surface 164 of the substantially rigid shell or case 130. As shown in FIG. 1C, a graphic user interface 166 may be operatively coupled to a controller 168, which may include at least one processor 170, a memory device 172 and connective circuitry or other data conduits that couple the data generating or data managing components of the device. A power storage cell in the form of a battery 174 that may be rechargable may also be disposed within the housing 124. Data generating or managing components of the device may include the processor(s) 170, the memory device 172, sensors 158, including any pressure or temperature sensors, the GUI 166 and the like.

Other components such as the vibratory motor 175, speaker 178, battery 174 and motor 152 of the drive mechanism 150 may also be operatively coupled to the controller 168. Connective circuitry may include conductive wiring such as copper wiring, fiber optic conduits, RF conduits and the like.

For the embodiment shown, the vent inlet port 146 may be disposed on the delivery mechanism 132 in fluid communication with the volume 160 disposed between the outside surface 162 of the flexible material or membrane 128 of the collapsible reservoir 126 and an inside surface 164 of the substantially rigid shell or case 130 of the infusion cartridge. The controller 168 may include at least one processor 170 and a memory device 172, the controller 168 being operatively coupled to the drive mechanism 150, GUI 166, and at least one pressure sensor 158. The controller may be configured to generate a signal to the drive mechanism 150 to displace the spool 156 of the delivery mechanism 132.

Figure 2:
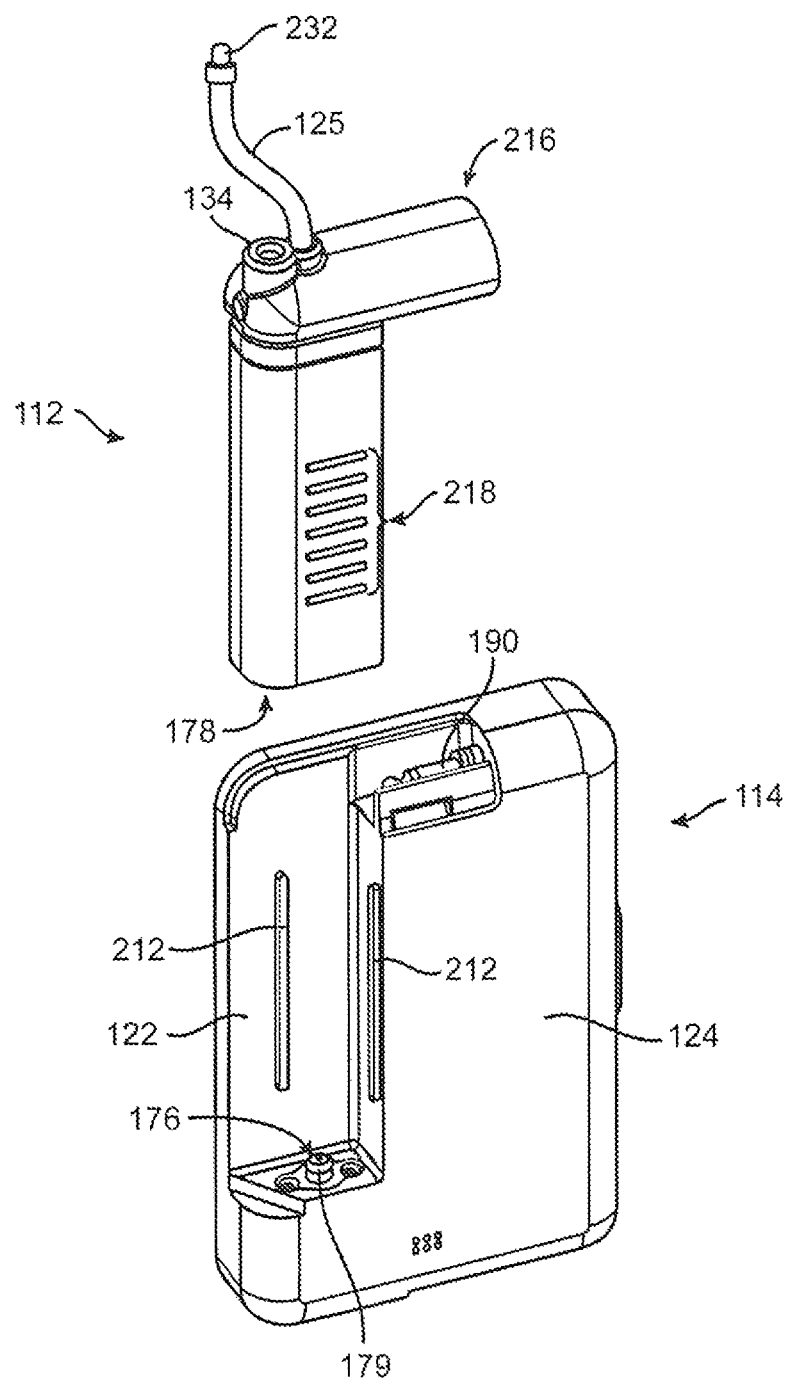
FIG. 2 depicts an exploded view of the infusion cartridge and pump of FIGS. 1A-1C.
Figure 3:
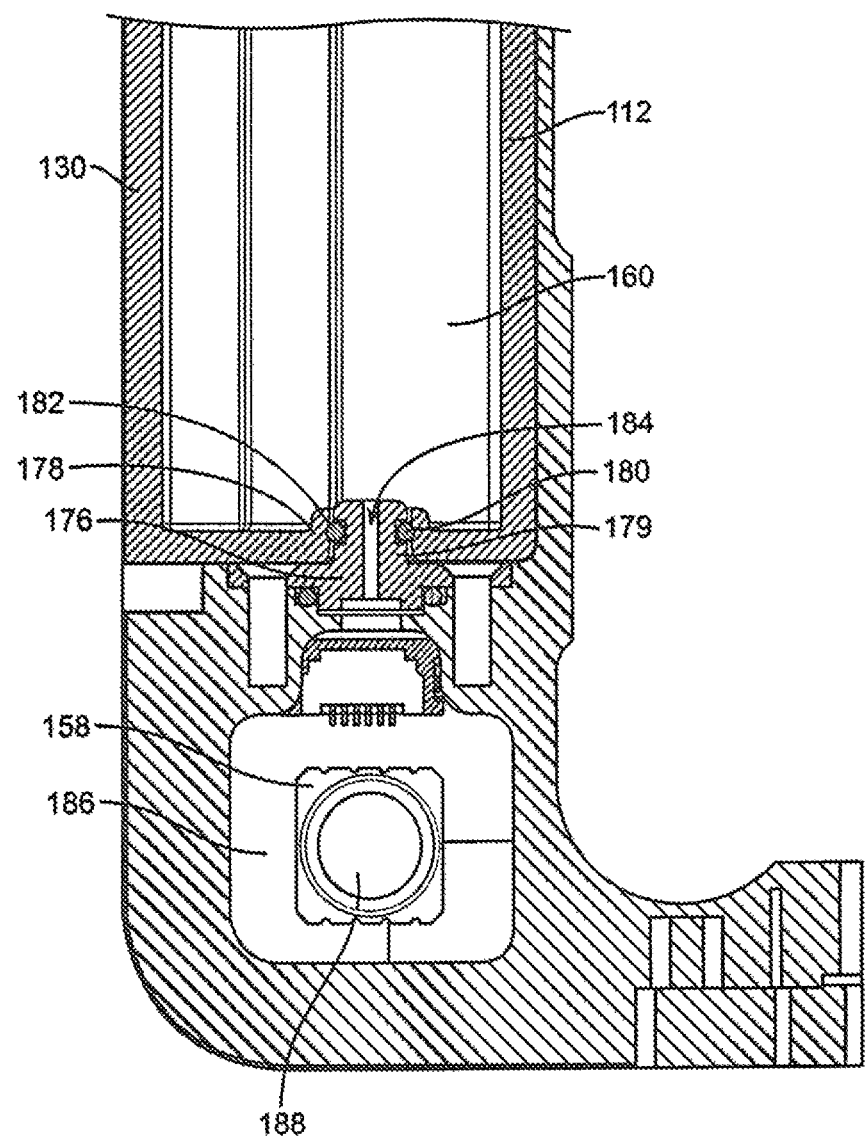
FIG. 3 depicts a section view of an attachment mechanism of the infusion cartridge and pump device of FIG. 2.

As shown in FIGS. 2-3, the pump device 114 may include an attachment mechanism 176 positioned within the slot 122 near its terminus that corresponds to a receiving mechanism 178 at an end of the infusion cartridge 112. The attachment and receiving mechanisms may be configured to removably couple an interior volume of the cartridge with a volume of the pump that is sealed from the surrounding environment with the coupling able to retain a fluid within the volumes even under significant pressure. The o-ring based tap attachment embodiment discussed below may be so configured and suitable for producing a leak free detachable coupling that can withstand significant pressure. The receiving mechanism 178 may be configured to detachably couple with the attachment mechanism 176 such that the infusion cartridge 112 may be reversibly attached to the housing 124 of the pump device 114 for fluid delivery. In these embodiments, the attachment mechanism 176 may include a pneumatic tap 179 having an o-ring 180 or other sealing device. The corresponding receiving mechanism 178 positioned on an end of the infusion cartridge 112 may include a port 182 through which the pneumatic tap 179 may be inserted.

The pneumatic tap 179 may include an inner channel 184 running therethrough. The channel 184 may allow the tap 179 to fluidly connect the inner chamber volume 160 of the infusion cartridge 112 to the pump device 114 once the tap 179 is inserted through the port. The inner channel 184 of the tap 179 may connect to a pocket 186 of the pump device 114 that may be filled with a fluid such as air. In some embodiments, the pocket 186 in the pump may hold approximately 1 mL of the air. When the fluid reservoir of the infusion cartridge may be filled with 3 mL insulin or other medicament a residual volume of the inner chamber may exist. This residual volume may be, for example, 1 mL of air. Upon connection between the infusion cartridge 112 and the pump device 114, the residual volume of air within the inner chamber on volume 160 and the air within the pocket 186 may equalize and equilibrate in both temperature and pressure. The volume of the pocket 186 and volume 160 of the cartridge may also be in sealed relation with respect to each other and with respect to the surrounding environment. Thus, the pressure within volume 160 will equalize with the pressure in the pocket 186, thus, the pressure or pressure changes within volume 160 may be measured by the pressure sensor 158 in the pocket 186.

The pump devices 114 and others described herein may include a thermistor or other temperature sensor 188 including an optical or infrared sensor that measures the temperature of the insulin or other medicament within the reservoir 126 upon coupling the infusion cartridge 112 with the pump device 114. Taking the temperature of the air may be important in measuring how much insulin or other medicament is in the fluid reservoir. In some embodiments, the sensor 188 can be integrated with the attachment mechanism 176. In some embodiments shown in FIGS. 1A-3, the pocket 186 may have a thermistor or other temperature sensor 188 positioned therein such that it can measure the temperature of the air in the pocket 186 as shown in FIG. 3. The pocket 186 may also include a pressure sensor 158 coupled to the controller 168 for measuring pressure within the pocket 186 and volume 160 Because the air in the pocket 186 is in fluid communication with the residual air within the chamber 160, the temperature and pressure of the air in the infusion cartridge 112 surrounding the fluid reservoir 126 may be equal or approximately equal to the temperature and pressure of the air in contact with the temperature sensor 188 and pressure sensor 158. In turn, the temperature sensor 188 may provide a relatively accurate measurement of the temperature of the insulin or other medicament within the reservoir 126.

The pressure inside the infusion cartridge 112, and particularly the interior volume 160 of the infusion cartridge 112, may be measured by a pressure sensor 158 disposed in the infusion cartridge 112 or in the pump device 114 in a volume, such as pocket 186. Pocket 186 is an interior volume disposed within the pump device 114 and in fluid communication with an interior volume of the fluid cartridge 112. The pocket 186 is in sealed relation with the interior volume 160 of the cartridge. As such, a pressure sensor 158 disposed within the volume of the pocket 186 will read the pressure of the volume 160 in the cartridge, but can remain with the pump device 114 after disposal of the disposable cartridge 112. This configuration lowers the cost of the cartridge while providing the means of pressure measurement within the cartridge 112. In some embodiments, data from the pressure sensor 158 may be used to provide a measurement of how much insulin or other medicament is being delivered by the first pump device 114.

Referring to FIGS. 4-7, an embodiment of a delivery mechanism 132 is depicted in a fluid delivery cycle sequence wherein fluid from the interior volume of the reservoir 126 is drawn into the bore 220 of the delivery mechanism 132 and dispensed from the dispense outlet port 142. The dispense cycle embodiment shown in FIGS. 4-7 illustrates a dispense cycle without a venting of the interior volume 160 of the infusion cartridge 112 of the pump system 110. FIG. 8 shows an optional venting step wherein a vent second volume 246 of the delivery mechanism 132 is disposed in communication with a vent inlet port 146 and a vent outlet port 148 of the delivery mechanism 132. The dispense and vent method embodiments discussed herein may also be combined with one or more methods and devices for measuring and/or confirming a volume of fluid dispensed or flow from a delivery mechanism 132. Venting of the volume of the shell 130 surrounding the reservoir may be useful, in order to prevent pressure buildup of the fluid in the reservoir 126 which might then force fluid 121 past seals of the system to a patient 127.

Referring again to FIG. 4, a portion of the fluid reservoir cartridge 112 including a delivery mechanism 132 is shown in section as well as a portion of a drive mechanism 150 of an infusion pump. The disposable fluid cartridge 112 includes the delivery mechanism 132 which has a delivery mechanism body 236 and a bore 220 disposed in the delivery mechanism body 236. The bore 220, which may have a substantially round transverse cross section, includes a distal end 238, a proximal end 240 disposed towards the drive mechanism 150 of the infusion pump 114, an interior volume 242, a reservoir inlet port 138, a fluid dispense port 142, a vent inlet port 146 and a vent outlet port 148. The spool 156, which may also have a substantially round transverse cross section, is slidingly disposed within the bore 220 and forms a collapsible first volume 244 and a vent second volume 246 with the bore 220.

The collapsible first volume 244 of the delivery mechanism 132 may be positionable to overlap the reservoir inlet port 138 independent of an overlap of tire fluid dispense port 142. The collapsible first volume 244 may be formed between a first seal 248 around the spool 156, a second seal 250 around the spool, an outer surface of the spool body between the first and second seal 250 and an interior surface 252 of the bore 220 between the first and second seal 248 and 250. The first and second seals 248 and 250 are axially moveable relative to each other so as to increase a volume of the collapsible volume 244 when the first and second seals 248 and 250 are moved away from each other and decrease the collapsible volume 244 when the seals 248 and 250 are moved closer together.

The second seal 250 is disposed on a main section 254 of the spool 156 of the delivery mechanism 132 and moves in conjunction with movement of the rest of the spool. A proximal end 256 of the spool 156 is coupled to a ball portion 194 of a drive shaft 190 of the drive mechanism 150 of the pump device 114. The drive mechanism 150 includes a rack and pinion mechanism actuated by an electric motor 152 through a gear box 154. As such, the second seal 250 moves or translates axially in step with axial translation of the spool 156 and drive shaft 190. The first seal 248, however, is disposed on a distal section 258 of the spool 156 which is axially displaceable with respect to the main section 254 of the spool 156. The distal section of the spool 156 is coupled to the main section of the spool by an axial extension 260 that is mechanically captured by a cavity 261 in the main section 254 of the spool 156. This configuration allows a predetermined amount of relative free axial movement between the distal section 258 of the spool and the nominal main section 254 of the spool 156.

For some embodiments, a volume of a "bucket" of fluid dispensed by a complete and full dispense cycle of the spool 156 may be approximately equal to the cross section area of the bore 220 multiplied by the length of displacement of the captured axial extension of the spool 156 for the distal section 258. The complete bucket of fluid may also be dispensed in smaller sub-volumes in increments as small as a resolution of the drive mechanism 150 allows. For some embodiments, a dispense volume or bucket defined by the complete collapsible volume 244 of the delivery mechanism 132 may be divided into about 10 to about 100 sub-volumes to be delivered or dispensed. In some eases, the maximum axial displacement between the distal section and main section of the spool may be about 0.01 inch to about 0.04 inch, more specifically, about 0.018 inch, to about 0.022 inch.

In some instances, a vent second volume 246 of the delivery mechanism 132 may be formed by the spool 156 and bore 220 of the delivery mechanism 132. For some embodiments, the vent second volume 246 may be formed by a third seal 262 disposed around the spool 156 and a fourth seal 264 also disposed around the spool and axially separated from the third seal 262. The axial separation between the third and fourth seals 262 and 264 forming the vent second volume 246 may be greater than the axial separation between the vent inlet port 146 and vent outlet port 148 of the bore 220 in some instances. The vent second volume 246 is also formed by an outside surface 266 of the spool 156 between the third and fourth seal 262 and 264 and an inside surface 252 of the bore 220 between the third and fourth seal 262 and 264.

The vent second volume 246 may be axially displaceable with the movement of the spool 156 and may also be positionable by such axial displacement in order to simultaneously overlap the vent second volume 246 with the vent inlet port 146 and vent outlet port 148 of the bore 220. Such an overlap of both the vent inlet port 146 and vent outlet port 148 puts these ports in fluid communication with each other and allows an equilibration of pressure between the volume 160 of the reservoir cartridge 112 and the environment surrounding the vent outlet port 148 as the volume 160 is vented. In most cases, the vent outlet port 148 will be in communication with the atmosphere and air will pass from the environment surrounding the vent outlet port 148, through the vent second volume 246 of the bore 220 and into the interior volume 160 to replace the fluid dispensed subsequent to the last vent cycle. When the vent inlet port 146 and vent outlet port 148 do not share a common volume formed by the spool and bore of the delivery mechanism 132, they are typically isolated and no venting of the interior volume takes place.

Figure 4:
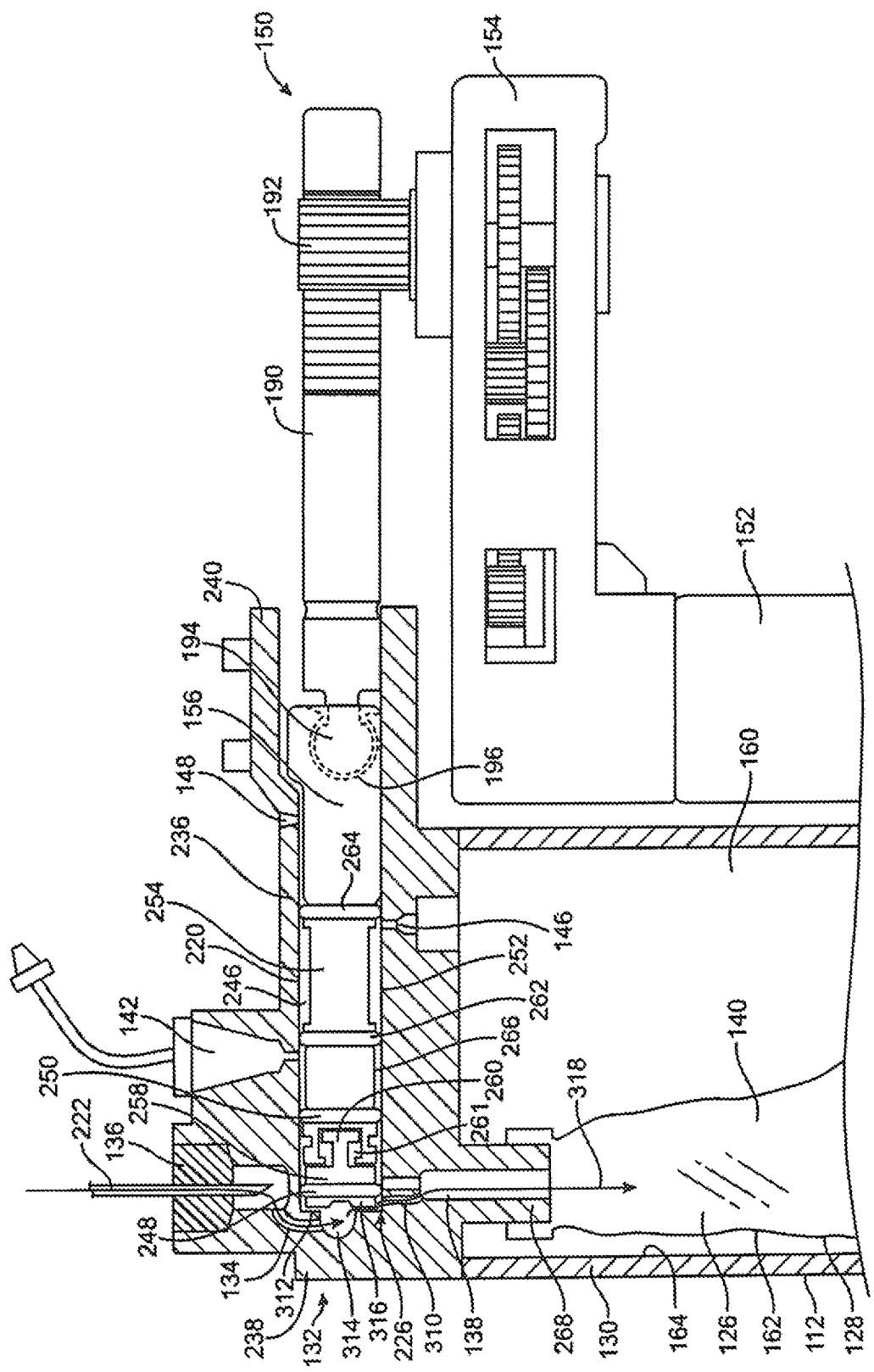
FIG. 4 is a section view of a delivery mechanism of a pump according to an embodiment of the present invention with the spool of the delivery mechanism positioned at a distal hard stop for filling of the expandable reservoir.

A collapsible fluid reservoir 126 of the infusion cartridge 112 shown in FIG. 4 may be bounded by or disposed within a flexible membrane or layer 128. The fluid reservoir 126 may include an interior volume 140 in fluid communication with the reservoir inlet port 138 of the bore 220 of the delivery mechanism 132. A top portion of the flexible membrane or layer 128 may be clamped or otherwise sealed to an extension or boss 268 of the reservoir inlet port 138 that extends into the cartridge 112. In this configuration, the interior volume 140 of the collapsible fluid reservoir 126 may be isolated or sealed from the surrounding environment except for the reservoir inlet port 138 which is in fluid communication with the bore 220 of the delivery mechanism 132. A substantially rigid shell 130 may be disposed about the collapsible fluid reservoir with an interior volume that contains the collapsible fluid reservoir. The interior volume 160 of the cartridge 112 is disposed between an outer surface 162 of the flexible membrane 128 and an interior surface 164 of the rigid shell 130. The vent inlet port 146 is in fluid communication with the interior volume 160 and the bore 220 of the delivery mechanism 132. The vent inlet port 146 is disposed proximally of the reservoir inlet port 138 for the embodiment of the delivery mechanism 132 shown.

In operation, the spool 156 and the particular volumes formed between the spool 156, the bore 220 and the circumferential seals 248, 250, 262 and 264 disposed on the spool of the delivery mechanism 132 are typically translated in a proximal and distal direction in order to move the volumes into and out of communication with the various ports of the bore 220. This axial movement in alternating proximal and distal directions of the spool 156 within the bore 220 may be used to put the various ports in fluid communication with translatable volumes of the delivery mechanism 132 and other ports of the mechanism. For reliable operation, it may be desirable in some circumstances for the spool 156 and the circumferential seals 248, 250, 262 and 264 disposed about the spool 156 to move smoothly within the bore 220 of the delivery mechanism 132 while maintaining a seal between an outside surface 266 of the spool 156 and an inside surface 252 of the bore. It may also be desirable for the seals 248, 250, 262 and 264 disposed on the spool 156 to move axially back and forth within the bore 220 while maintaining a seal and with a minimum of friction.

Once the reservoir cartridge 112 of the infusion pump system 110 has been installed or otherwise snapped into place in the slot 122 of the pump device 114, the interior volume 140 of the collapsible reservoir 126 may then be filled with a desired fluid 121 for dispensing. In order to fill the reservoir 126, the spool 156 may be translated by the drive mechanism 150 to a hard stop position 226 as shown in FIG. 4. In the hard stop position 226 the first seal 248 is disposed proximally of a relief port 310, the relief port 310 being disposed in fluid communication between a distal end 238 of the bore 220 and the reservoir volume 140. In the hard stop position, the first seal 248 is also disposed distally of the reservoir inlet port 138. In the hard stop position, a distal end 316 of the spool 156 is contacting a distal end 238 or shoulder portion 312 of the distal end 238 of the bore 220 to prevent any further distal displacement of the spool 156.

A reservoir fill port 134 is disposed on a top portion of the bore 220 substantially opposite the bore 220 of the reservoir inlet port 138. With the spool 156 and seals 248, 250, 262 and 264 thereof so positioned, a patient may then obtain an amount of a desired fluid to be dispensed. In some cases, if the desired fluid to be dispensed is insulin or other suitable medicament, the patient 127 typically stores the insulin in a refrigerated glass container. The insulin is then accessed with a hypodermic needle 222 of a syringe device and drawn into an interior volume of the syringe (not shown). The tip of the hypodermic needle 222 of the syringe may then be pushed through a septum membrane 136 that seals the reservoir fill port 134 as shown and fluid manually dispensed from the interior volume of the syringe, through the hypodermic needle 222, through a bubble trap volume 314 in the bore 220 of the delivery mechanism 132 and into the interior volume 140 of the collapsible reservoir 126 of the cartridge 112 as shown by the arrow 318 in FIG. 4.

As discussed above with regard to other embodiments of the delivery mechanism 132, the volume 160 of the cartridge 112 disposed between an outside surface 162 of the flexible membrane 128 of the collapsible reservoir 126 and an inside surface 164 of the rigid shell 130 may include or be in operative communication with a pressure sensor 158 (not shown). The pressure sensor 158 may be used to monitor the pressure within the Interior volume 160 during the filling of the collapsible reservoir 126. The controller 168 of the pump system 114 may be programmed with information regarding the fixed volume of the rigid shell 130 of the cartridge 112 and configured to calculate the volume of fluid loaded into the collapsible reservoir 126 based on the pressure rise within the rigid shell 130 upon filling of the collapsible reservoir 126. The data regarding the volume of fluid loaded into the collapsible reservoir 126 may be stored and used to calculate and display data later in the use cycle such as fluid remaining in the collapsible reservoir 126 and the like.

Once the collapsible reservoir 126 contains a desired amount of a fluid 121 to be dispensed, a dispense cycle may be initiated by driving the spool 156 with the drive mechanism 150 based on commands from a controller 168 of the pump device to a position with the collapsible first volume 244 in communication with the reservoir inlet port 138. The hard stop position shown in FIG. 4 is such a position. If the spool 156 has been driven to this hard stop position 226 in a distal direction from previous proximal position, the friction generated between the first seal 248 of the spool 156 and the inside surface 252 of the bore 220 will have collapsed the collapsible volume 244 of the delivery mechanism 132 with the first seal 248 and second seal 250 in a least axially separated state. In this state, the collapsible volume 244 has a minimum volume. Such a state of the delivery mechanism 132 is shown in FIG. 4. Once in this pre-fill position, the spool 156 may then be driven so as to axially separate the first and second seals 248 and 250 (and the main section 254 of the spool 156 and distal section 258 of the spool 156) of the collapsible first volume 244 and draw fluid into the first volume 244 through the reservoir inlet port 138 from the reservoir 126 as shown by the arrow 320 in FIG. 5. As the fluid 121 is drawn into the collapsible volume 244, the pressure within the interior volume 160 decreases. As previously discussed, this drop in pressure may be used in accordance with the ideal gas law to determine the amount of material taken from the collapsible reservoir 126. An unexpected reading based on the magnitude of the translation of the main section 254 of the spool 156 may also be used to detect a failure of a portion of the delivery mechanism 132 in some cases.

Figure 5:
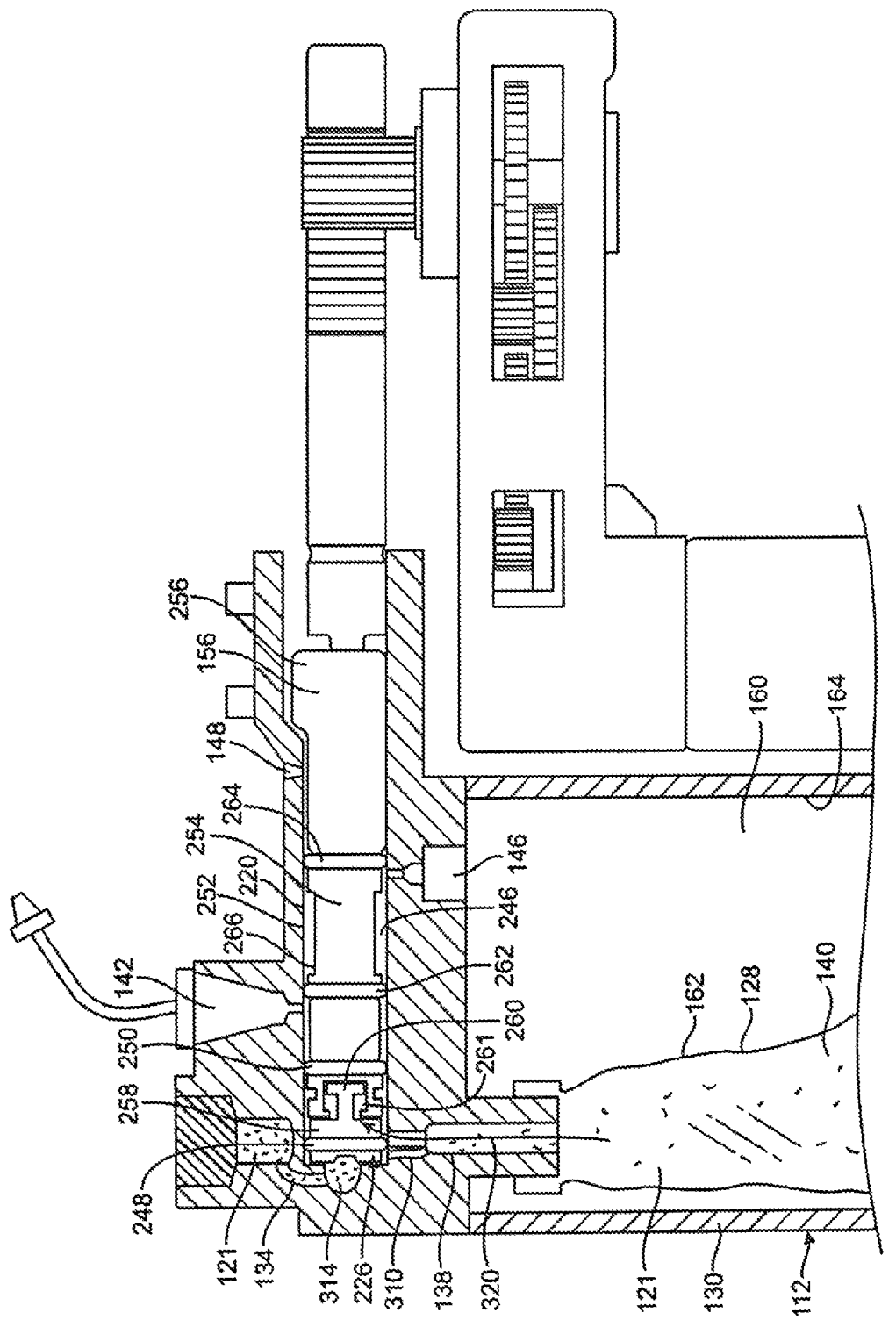
FIG. 5 is a section view of the delivery mechanism embodiment of FIG. 4 with the spool of the delivery mechanism positioned for filling of a collapsible volume of the spool.
Figure 5A:
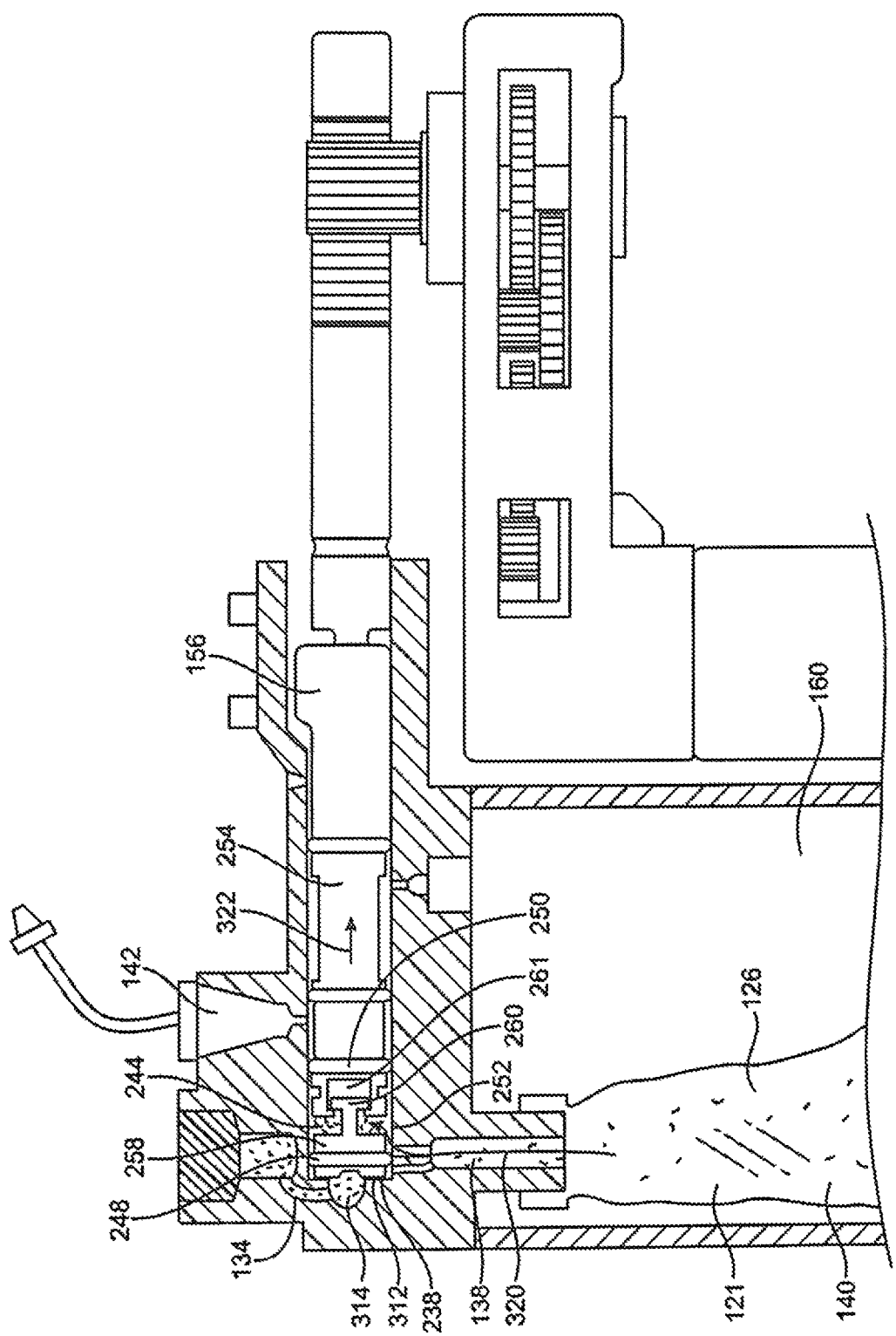
FIG. 5A is a section view of the delivery mechanism embodiment of FIG. 4 with the spool of the delivery mechanism positioned after filling of the collapsible volume of the spool.
Figure 5B:
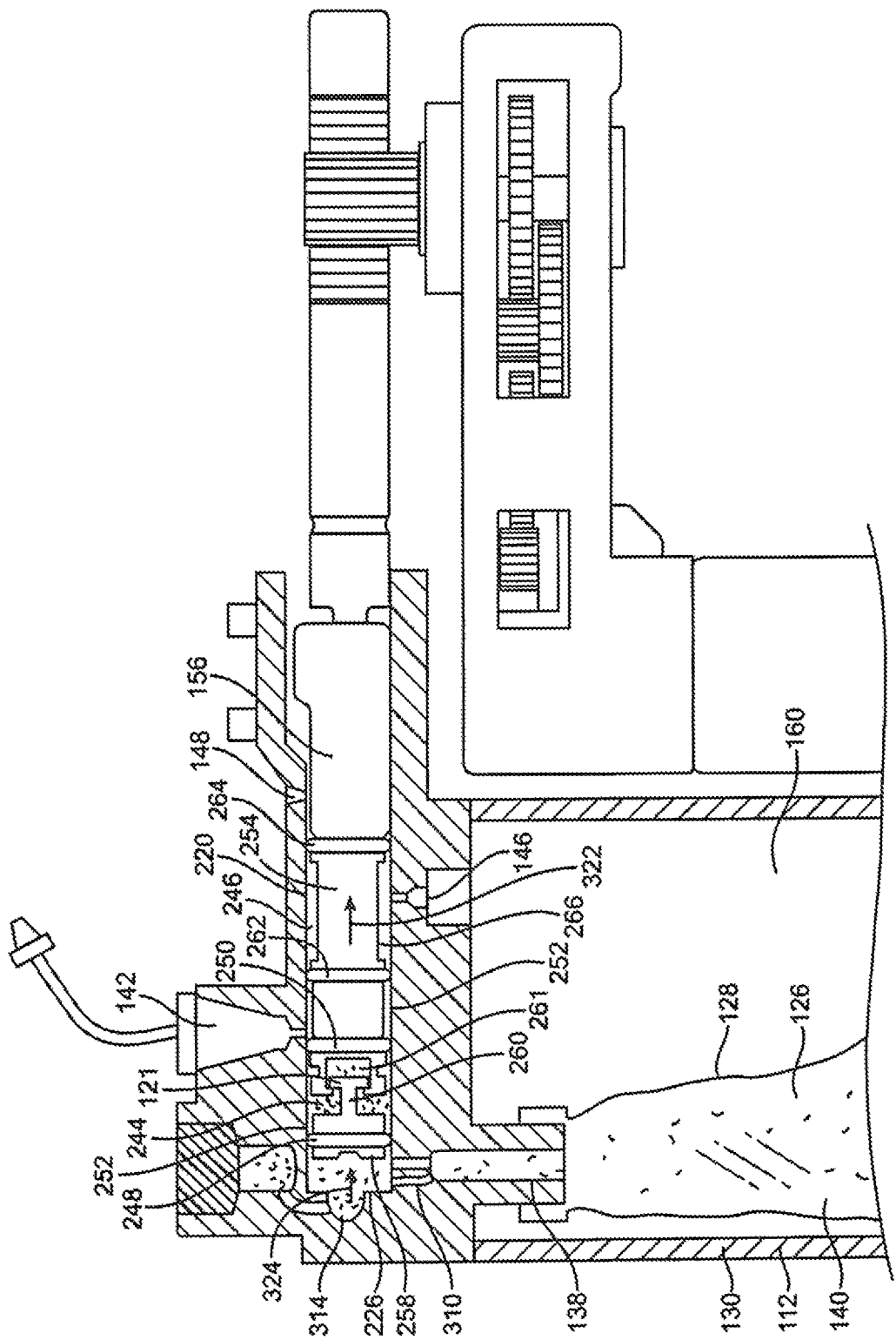
FIG. 5B shows the spool of FIG. 5A with the collapsible volume of the device full of fluid being displaced proximally towards the dispense port of the device.

The collapsible volume 244 of the delivery mechanism 132 may be completely filled by proximally retracting the main section 254 and second seal 250 of the spool 156 relative to the first seal 248 and distal section 258 of the spool 156 as shown by arrow 322 on spool 156 in FIG. 5A. Once filled, the spool 156 may then be driven in a proximal direction as shown in FIG. 5B wherein there are two seals 248 and 250 disposed in the bore 220 between the reservoir inlet port 138 and relief port 310 and the dispense port 142. As shown by arrow 322 and arrow 324 in FIG. 5B, both the main section 254 and distal section 258 of the spool 156 are proximally retracted together. The captured axial extension of the distal section 258 by the main section 254 pulls the distal section along without axial displacement between the main section 254 and distal section 258 of the spool 156. The dispense port may be in fluid communication with a subcutaneous portion of a patient's body 127 as shown in FIGS. 9D and 9E. The delivery mechanism 132 configuration illustrated in FIGS. 4-8 always includes at least one seal 248 or 250 disposed in the bore 220 between the reservoir volume 140 and material 121 disposed therein and the dispense port 142 in order to prevent a free flow condition wherein the material 121 in the reservoir 126 is in uninterrupted communication with the patient's body 127.

Figure 6:
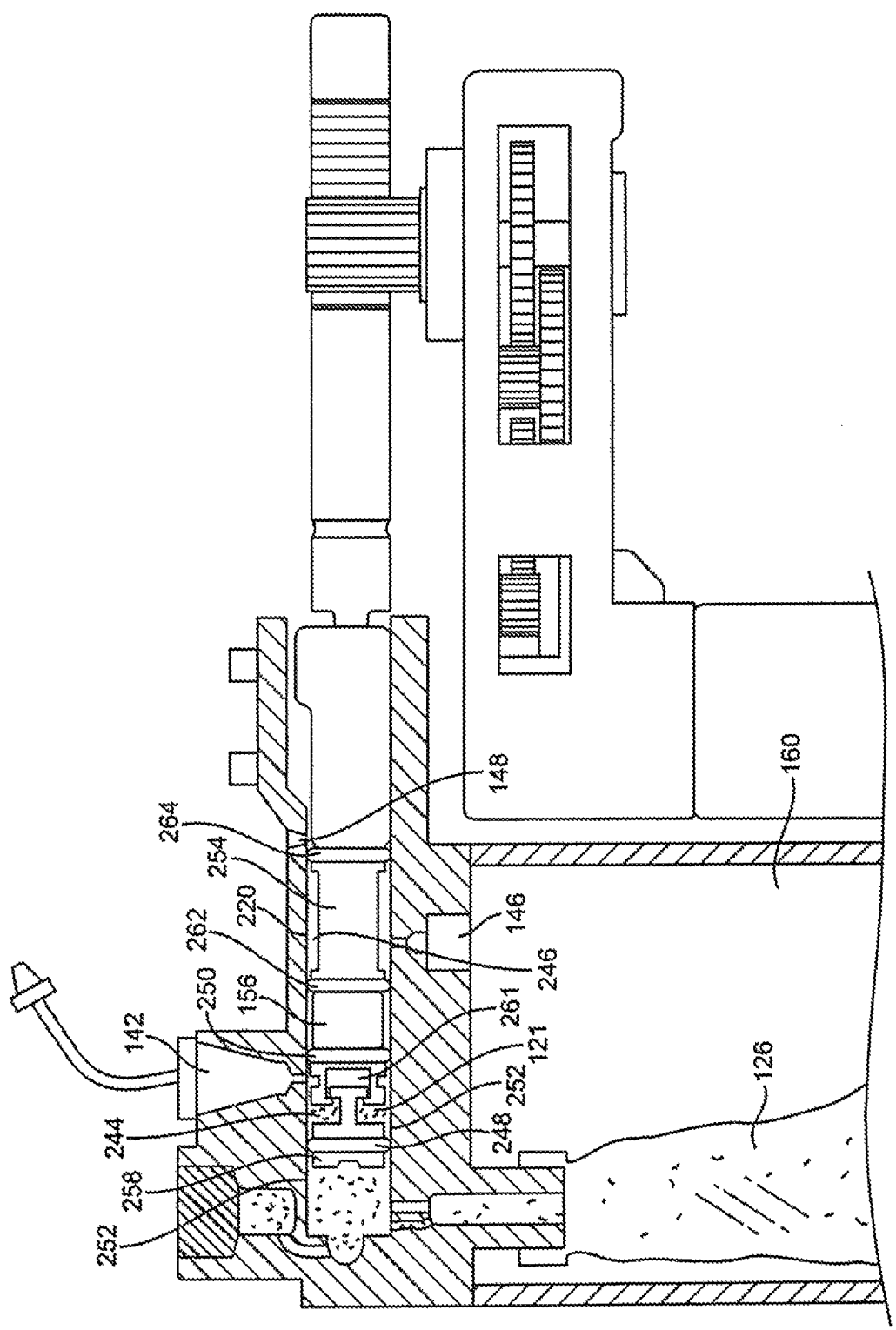
FIG. 6 is a section view of the delivery mechanism embodiment of FIG. 4 with the spool of the delivery mechanism positioned prior to delivery of fluid into the dispense port from the collapsible volume of the spool.
Figure 7:
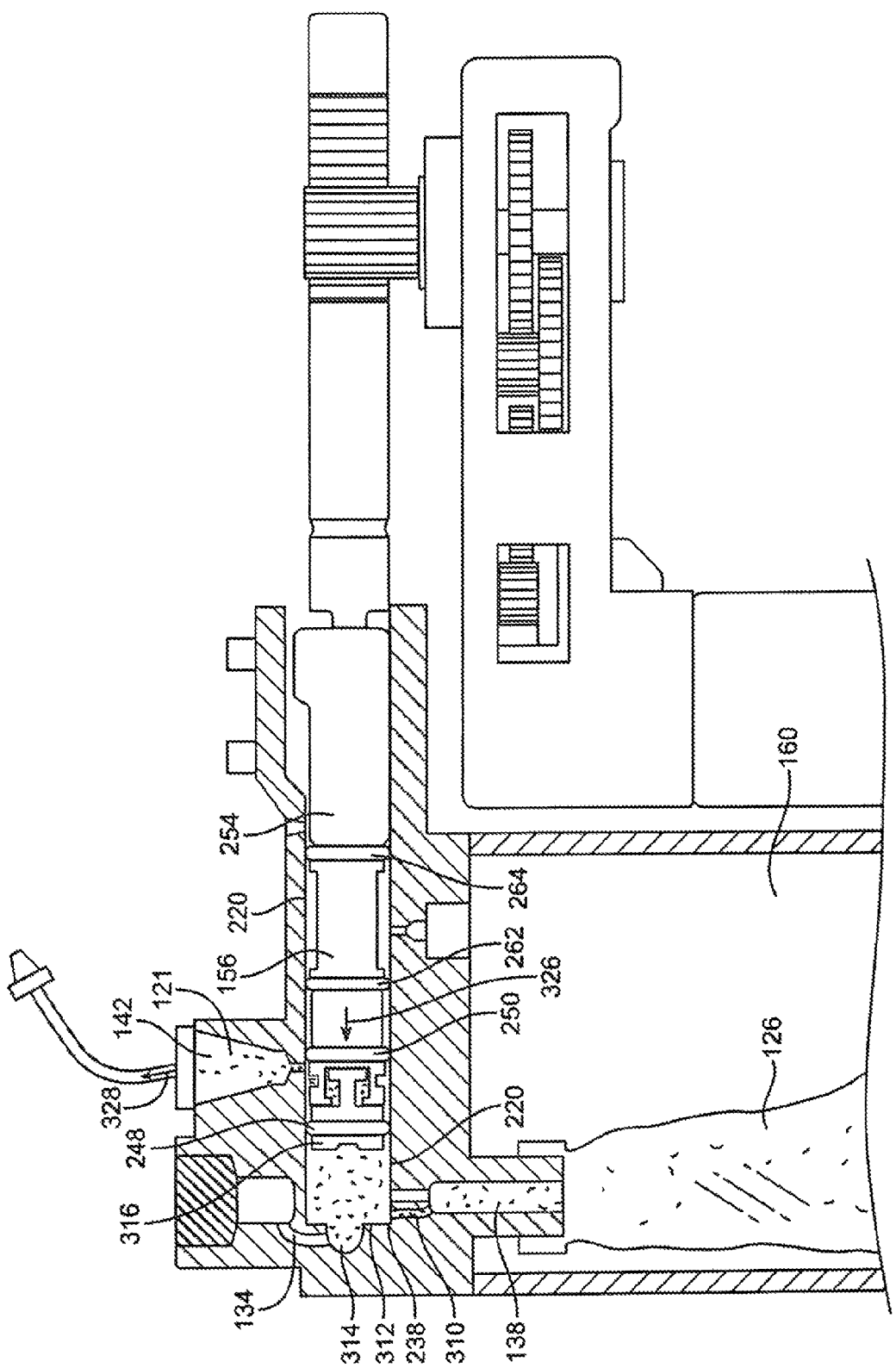
FIG. 7 is a section view of the delivery mechanism embodiment of FIG. 4 with the spool of the delivery mechanism positioned after delivery of fluid from the collapsible volume of the spool into the dispense port.

Once filled, the spool 156 and filled collapsible volume 244 may be proximally displaced with the drive mechanism 150 to a position with the collapsible first volume 244 in communication with the fluid dispense port 142 of the bore 220 as shown in FIG. 6. In the configuration shown in FIG. 6, the collapsible first volume 244 of the delivery mechanism 132 is in fluid communication with the fluid dispense port 142, but the vent second volume 246 is only in fluid communication with the vent inlet port 146 and not the vent outlet port 148. Thus, in the position shown, the spool 156 of the delivery mechanism 132 is configured to dispense the fluid 121 in the collapsible volume 244 without venting of the interior volume 160 of the cartridge 112. This arrangement allows one or more dispense cycles to be carried out independent of venting of the Interior volume 160.

Once the spool 156 is positioned as shown in FIG. 6, the main section of the spool 156 may then be axially driven in a distal direction by the drive mechanism 150 with the distal section 258 of the spool remaining stationary or substantially stationary. This axial distal movement of the main section 254 as indicated by arrow 326 on the spool 156 shown in FIG. 7, serves to at least partially collapse the collapsible first volume 244. Collapsing the first volume 244 of the delivery mechanism 132 dispenses fluid from the collapsible first volume 244 through the fluid dispense port 142 as shown by the arrow 328 in FIG. 7. For some embodiments, the axial distance of the translation between the first seal 248 and second seal 250 may be about 0.015 inches to about 0.025 inches. In some instances, the bore 220 may have an inner transverse dimension or diameter of about 0.10 inches to about 0.20 inches.

Figure 8A:
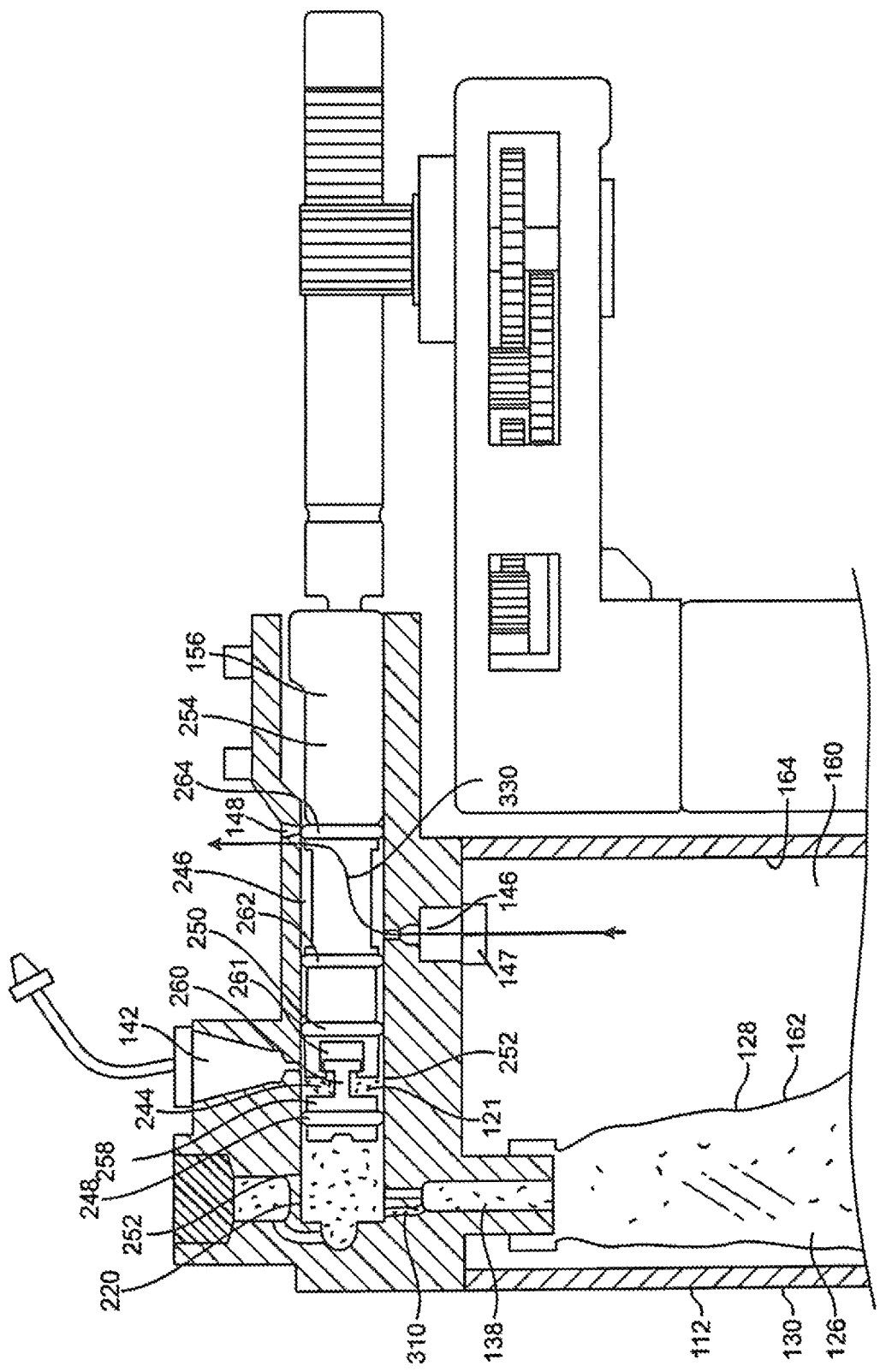
FIG. 8A is a section view of the delivery mechanism embodiment of FIG. 4 with the spool of the delivery mechanism positioned prior to delivery of fluid from the expandable volume of the spool and with a vent channel established for the interior volume of the cartridge.

After filling of the collapsible volume 244 of the delivery mechanism 132 as shown in FIG. 6, if venting of the interior volume 160 is desired, the spool 156 may be driven by the drive mechanism 150 to a position with the vent second volume 246 in simultaneous communication with the inlet vent port 146 and vent outlet port 148 as shown in FIG. 8A. This arrangement allows the interior volume 160 of the reservoir cartridge 112 to vent as shown by the arrow 330 in FIG. 8A. In such circumstances, the vent second volume 234 arrives at the same pressure as the vent outlet port 148 and interior volume 160. In some instances, the vent outlet port 148 may be at ambient atmospheric pressure and the interior volume 160 is brought to ambient atmospheric pressure during every venting cycle.

In some cases, the inferior volume 160 of the cartridge is vented about every 2 dispense cycles to about every 10 dispense cycles. In some cases, the interior volume 160 may be vented about every 3 dispense cycles to about every 7 dispense cycles. In some cases, the interior volume 160 may be vented almost every dispense cycle. However, any desired interval of venting cycles to dispense cycles may be used. For some embodiments, the venting of the interior volume 160 of the infusion cartridge 112 may be triggered by the detection or measurement of a pressure difference threshold in the interior volume 160. That is, if the pressure measured in the interior volume 160 of the infusion cartridge 112 is above or below a predetermined valued relative to the ambient pressure, the controller 168 will initiate a venting cycle to vent the interior volume 160 and equalize the pressure in the interior volume 160. For some embodiments, the magnitude of such a threshold pressure difference may be up to about 1 psi gauge, more specifically, up to about 0.1 psi gauge. In some embodiments, the threshold pressure difference, or threshold value, may be about 0.5 psi gauge, or alternatively, the threshold value may be about 0.25 psi gauge.

In some cases, the interior volume 160 is vented during periods when the drive mechanism 150 is not active and the volume is temporarily sealed when a pressure based measurement is required, such as at times before and/or after the pump device delivers and/or has delivered fluid. In such cases, the interior volume 160 may be sealed through positioning of the spool 156; use of a valve 147 (FIG. 8A), such as, for example, a solenoid valve, or, alternately, through positioning of the spool 156 and use of a valve 147. The valve 147 may be in any suitable location in the cartridge 112 or pump housing 124 to interrupt communication between the interior volume 160 and the ambient environment. The valve 147 may control the flow of air or other gases through the vent inlet port 146 or the vent outlet port 148. The valve 147 can be adjacent to the vent inlet port 146. The valve may be located within the Interior volume 160 as shown in FIG. 8A or within the rigid shell 130 of the cartridge when adjacent to the vent inlet port 146. Alternatively, the valve 147 can be adjacent to the vent outlet port 148. In such configurations, the vent 147 may be located outside the rigid shell 130 of the cartridge. The valve 147 may open or close to vent or seal the interior volume in response to user input from the user interface, a button, a dial, a knob, or the like. A controller may open or close the valve 147 based on previously entered threshold information, programs, data received from other parts of the infusion pump system, etc.

An exemplary manner in which temporary sealing is utilized is described as follows. First, the pump device indicates to the drive mechanism 150 that a fluid dispense cycle is about to start. The spool 156 of the delivery mechanism 132, or a valve 147, seals the interior volume 160. A pressure sensor measures the pressure in the interior volume 160 once the interior volume is sealed. The delivery mechanism 150 dispenses the required amount of fluid. The required amount of fluid may be equivalent to one or more dispense strokes (i.e., action that causes translation of the spool 156 to cause withdrawal of fluid from the reservoir 126 and expulsion of fluid into the dispense port 142) of the drive mechanism 150. After the drive mechanism 150 completes the final stroke to deliver the required amount of fluid, the pressure sensor measures the pressure within the interior volume 160 again. The difference in pressure readings before and alter the drive mechanism 150 dispenses the fluid is used by the pump device to calculate the amount of fluid dispensed. The interior volume 160 is unsealed after the pressure sensor determines the end pressure. The end pressure is the pressure in the interior volume 160 after the drive mechanism 150 dispenses the desired amount of fluid. A valve 147 may open to unseal the interior volume 160 after the pressure sensor has determined the end pressure. Alternatively, the spool 156 may move into a position that allows the interior volume 160 to unseal after the end pressure is determined. The interior volume 160 may also be temporarily sealed by the spool 156 position or a valve 147 when fluid is added to the reservoir 126 so that pressure readings can be measured before and after fluid is added, allowing the pump device to calculate the amount of fluid added.

Figure 8B:
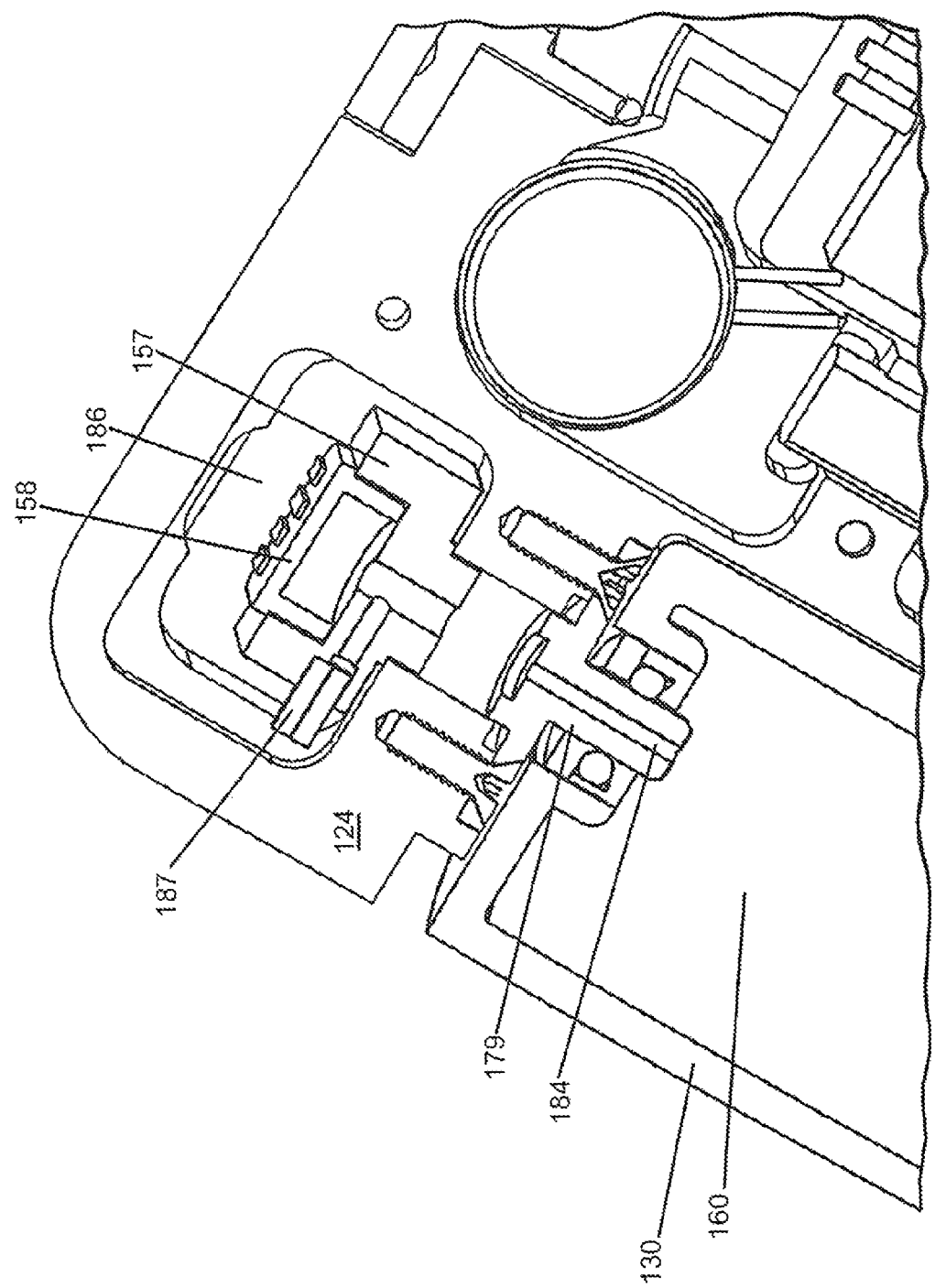
FIG. 8B is a section view of one embodiment in which the volume surrounding the reservoir in the infusion cartridge is vented in a passive manner.

In some embodiments, a passive mechanism may vent the volume surrounding the collapsible reservoir 126 (i.e. the interior volume 160) as shown in FIG. 8B. FIG. 8B depicts an infusion cartridge with a housing 130 interfacing with the pump housing 124 at the pneumatic tap 179. The infusion cartridge has a volume 160 that may passively be vented to allow the pressure inside the volume 160 to approach or reach equilibrium with the ambient pressure. The volume 160 shown in FIG. 8B communicates with the pressure sensor 158 in the pocket 186 within the pump housing 124 through the inner channel 184 within the pneumatic tap 179. The pressure sensor 158 is held in place within the pocket 186 by the pressure sensor isolator mount 157. The pressure sensor isolator mount 157 allows for fluid communication between the inner channel 184 of the pneumatic tap 179 and the pocket volume 186 via channels or orifices within the isolator mount 157. Connected to one of these channels or orifices is the capillary tube orifice 187. The capillary tube orifice 187 allows for communication ultimately between a portion of the pump housing 124 that may be in equilibrium (or nearly in equilibrium) with the ambient atmosphere and the interior volume 160.

In embodiments similar to those shown in FIG. 8B, the passive mechanism may include a passageway between the ambient environment and the interior volume 160 that is formed using micro-capillary tubing. In some cases the micro-capillary tubing may be about 30 µm in inner diameter and about 3 mm in length. The inner diameter and length of the micro-capillary tubing may be tailored to control the rate at which the interior volume equilibrates to ambient pressure after fluid is withdrawn or added to the reservoir. The inner diameter of the micro-capillary tubing may be about 100 µm or less, such as about 75 µm or less, such as about 50 µm or less, including about 30 µm or less. In some cases, more than one passageway may be used to passively vent the interior volume 160. In such cases, each of the passageways may include micro-capillary tubing that is tailored in at least an inner diameter such that cumulatively the rate of venting through the passageways allows the pump device accurately to measure the pressure within the interior volume 160.

In some embodiments, the passive venting configuration allows the interior volume 160 to equilibrate with the ambient atmosphere after about 30 seconds, such as after about 60 seconds, or after about 90 seconds. In such cases, each passageway in the passive venting configuration may be configured such that the minimum amount of time for the interior volume 160 to equilibrate with the ambient atmosphere is at least about 30 seconds, such as about 60 seconds or even about 90 seconds. The time for the interior volume 160 to equilibrate with the ambient atmosphere in some passive venting configurations may be less than 30 seconds. In some cases, the passive venting configuration allows the interior volume 160 to equilibrate with the ambient atmosphere in an amount of time less than about 5 minutes, such as less than about 4 minutes, or less than about 3 minutes.

Such timing allows accurate pressure readings to be taken before and after a backstroke without subjecting the reservoir to undesirable pressurization for extended periods of time. The controlled passive venting may be slow enough that the pressure reading taken after a fluid dispense or series of dispense actions may be still representative of the pressure in the interior volume 160 right after the fluid dispense. The ability for the system to take a pressure reading that reflects the pressure in the volume 160 immediately after the dispense of fluid influences the operation of the system in the cases in which the change is pressure (i.e. the pressure reading before and after the dispense) is used to calculate a change in volume, as described in greater detail elsewhere herein.

Micro-capillary tubing that is part of passive venting configurations may be fabricated from glass that is drawn to achieve the desired inner diameter, cut to length, and then polished. The glass used may be any suitable glass, such as a soda-lime glass, borosilicate glass, E-glass, S-glass or silica. The material used to make the micro-capillary tubing may also be any material that can be drawn to produce a suitable inner diameter, including a polymer or an inorganic material. Inorganic materials that may be used include metals, such as aluminum alloys, semiconductors, and metal oxides, such as sapphire and other aluminum oxides ($Al_2O_3$). Polymers which may be used to form micro-capillary tubing include polyamides (nylons), polyesters, polyethylene, polystyrene and poly (vinyl chloride) (PVC). Micro-capillary tubing may be formed by processes other than those which employ drawing techniques. Such processes may include etching process and growth processes which form structures with the appropriate inner diameter that may be included into the passageways of the passive venting configurations. A length of micro-capillary tubing is placed into a passageway in a passive venting configuration and sealed, or affixed, using any suitable adhesive or compound, such as UV curing epoxy.

Each passageway that allows for passive venting of the interior volume 160 may directly terminate at one end at the outer surface of the cartridge 112. Alternatively, each passageway that allows for passive venting of the interior volume may communicate with the ambient environment through a protected interface, such as an orifice that is covered by a selectively permeable material, such as polytetrafluoroethylene (PTFE) or expanded polytetrafluoroethylene (ePTFE). In some cases, a passage that includes a length of micro-capillary tubing leads from the interior volume 160 to an opening in the pump device that is used for audio communication. The opening that is used for audio communication may be sealed with PFTE, ePTFE, or semi-permeable membrane made from a different suitable material. Such configurations allow the passageway to be continuously in communication with the ambient environment, and thus allow the interior volume to equilibrate with ambient pressure, while reducing the likelihood that the passageway will become occluded or damaged.

Each passageway that allows for passive venting of the interior volume 160 communicates with the interior volume. Such communication may be established by originating the passageway in the interior volume 160, such as at the interior surface of the cartridge 112. Each passageway may be in communication with a volume that is fluidly connected to the interior volume 160, such as a volume that communicates with the interior volume via the pneumatic tap 179. Such volumes include volumes within the manifold, adjacent to the interior pressure sensor 158.

The use of a passive mechanism to vent the volume within the cartridge surrounding the reservoir (i.e., interior volume 160) may be used with or without an active mechanism to vent the volume 160. An active venting mechanism may include a valve 147 adjacent the vent portion of the spool 156 as shown in FIG. 8A. When used alone, a passive mechanism obviates the need for certain portions of the delivery mechanism 132, including certain o-rings and segments of the bore 220, such as the vent inlet port 146 and vent outlet port 148. In cases where an active venting mechanism is used in conjunction with a passive venting mechanism, the active venting mechanism may actuate in response to a difference in pressure between the inside of the cartridge 112 and the ambient pressure. In such cases, the difference in pressure that causes the active venting mechanism to actuate may be about 0.25 psi gauge or greater, such as about 0.3 psi gauge or greater, including about 0.4 psi gauge or greater, or about 0.5 psi gauge or greater.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

The invention claimed is:
1. An ambulatory infusion system, comprising:
a fluid cartridge including a collapsible reservoir for containing a fluid and a substantially rigid shell disposed over the collapsible reservoir and forming an interior volume between an outside surface of the collapsible reservoir and an inside surface of the shell;
a delivery mechanism including a spool member at least partially disposed in a bore defined in the fluid cartridge, the bore defining an interior volume;
a pump device configured to selectively receive the fluid cartridge and cooperate with the delivery mechanism to deliver fluid from the reservoir to a patient;
a vent inlet port defined in the fluid cartridge extending between the interior volume of the fluid cartridge and the interior volume of the bore;
a vent outlet port defined in the fluid cartridge extending between the interior volume of the bore and an exterior of the fluid cartridge; and
a selectively closeable valve disposed between the interior volume of the fluid cartridge and the exterior of the fluid cartridge, wherein the valve is selectively closeable to control flow of air through one or more of the vent inlet port and the vent outlet port.

2. The ambulatory infusion system of claim 1, wherein the valve is disposed in the interior volume of the fluid cartridge adjacent the vent inlet port.

3. The ambulatory infusion system of claim 1, wherein the valve is disposed within the vent inlet port.

4. The ambulatory infusion system of claim 1, wherein the valve is disposed in the interior volume of the bore adjacent the vent inlet port.

5. The ambulatory infusion system of claim 1, wherein the valve is disposed in the interior volume of the bore adjacent the vent outlet port.

6. The ambulatory infusion system of claim 1, wherein the valve is disposed in the vent outlet port.

7. The ambulatory infusion system of claim 1, wherein the valve is disposed on the exterior of the fluid cartridge adjacent the vent outlet port.

8. The ambulatory infusion system of claim 1, further comprising a user interface, and wherein the valve is selectively opened and closed in response to input received at the user interface.

9. The ambulatory infusion system of claim 1, further comprising a processor that controls system operation, and wherein the valve is automatically opened and closed by the processor in response to a sensed condition of the system.

10. The ambulatory infusion system of claim 8, further comprising a sensor disposed in one of the fluid cartridge and the pump adapted to obtain pressure measurements in the interior volume of the fluid cartridge, and wherein the processor closes the valve to obtain a pressure measurement with the sensor.

11. The ambulatory infusion system of claim 1, wherein the valve is a solenoid valve.

12. An infusion pump system, comprising:
a pump device including a housing, a drive mechanism with a motor, and a controller operatively coupled to the drive mechanism;
a fluid cartridge operatively coupleable to the housing, the fluid cartridge including a delivery mechanism, a collapsible reservoir having an interior volume surrounded by a flexible fluid tight membrane, the interior volume being in fluid communication with a reservoir inlet port, the fluid cartridge also comprising a substantially rigid shell disposed over the reservoir and forming a second interior volume between an outside surface of the reservoir and an inside surface of the rigid shell;
a pressure sensor configured to obtain pressure measurements of the second interior volume of the fluid cartridge between the inside surface of the rigid shell and the outside surface of the reservoir;

a bore within a body of the delivery mechanism, the bore defining the reservoir inlet port and a vent inlet port in communication with the second interior volume of the fluid cartridge and a dispense port and a vent outlet port in communication with an exterior of the fluid cartridge;

a spool slidingly disposed in the bore having a collapsible first volume which is configured to communicate with the reservoir inlet port and the dispense port of the bore independently of each other, the spool further defining a vent second volume positionable to overlap the vent inlet port and the vent outlet port simultaneously; and a selectively openable and closeable valve disposed between the second interior volume of the fluid cartridge and the exterior of the fluid cartridge, wherein the valve is selectively closeable to control flow of air through one or more of the vent inlet port and the vent outlet port.

13. The system of claim 12, wherein the pressure sensor is configured to measure small changes in pressure at low pressures.

14. The system of claim 13, wherein the pressure sensor is configured to measure pressures up to about 30 psi.

15. The system of claim 14, wherein the pressure sensor is configured to measure pressures up to about 5 psi.

16. The system of claim 12, further comprising a user interface, and wherein the valve is selectively opened and closed in response to input received at the user interface.

17. The system of claim 12, wherein the controller automatically opens and closes the valve in response to a sensed condition of the system.

18. The system of claim 17, wherein the controller closes the valve to obtain a pressure measurement with the sensor.

19. The system of claim 12, wherein the valve is disposed in a location selected from the group consisting of:
   in the second interior volume of the cartridge adjacent the vent inlet port;
   within the vent inlet port;
   in the collapsible first volume adjacent the vent inlet port;
   in the collapsible first volume adjacent the vent outlet port;
   in the vent outlet port; and
   on the exterior of the fluid cartridge adjacent the vent outlet port.

20. The system of claim 12, wherein the pressure sensor is disposed in the pump device.

* * * * *